United States Patent
Atiya et al.

(10) Patent No.: US 9,660,418 B2
(45) Date of Patent: May 23, 2017

(54) VCSEL BASED LOW COHERENCE EMITTER FOR CONFOCAL 3D SCANNER

(71) Applicant: Align Technology, Inc., San Jose, CA (US)

(72) Inventors: Yossef Atiya, Maccabim (IL); Tal Verker, Ofra (IL)

(73) Assignee: ALIGN TECHNOLOGY, INC., San Jose, CA (US)

( * ) Notice: Subject to any disclaimer, the term of this patent is extended or adjusted under 35 U.S.C. 154(b) by 209 days.

(21) Appl. No.: 14/470,832

(22) Filed: Aug. 27, 2014

(65) Prior Publication Data
US 2016/0064898 A1    Mar. 3, 2016

(51) Int. Cl.
*G01C 11/12* (2006.01)
*H01S 5/183* (2006.01)
(Continued)

(52) U.S. Cl.
CPC .............. *H01S 5/183* (2013.01); *F21V 5/04* (2013.01); *G01B 11/0608* (2013.01);
(Continued)

(58) Field of Classification Search
CPC .. G01N 21/274; G01N 21/474; G01N 21/359; G01N 2201/129; G01N 21/6428;
(Continued)

(56) References Cited

U.S. PATENT DOCUMENTS 2,467,432 A    4/1949 Kesling
3,407,500 A    10/1968 Kesling
(Continued)

FOREIGN PATENT DOCUMENTS

AU    3031677 A    5/1979
AU    517102 B2    7/1981
(Continued)

OTHER PUBLICATIONS

International search report and written opinion dated Feb. 12, 2016 for PCT/IB2015/001449.
(Continued)

*Primary Examiner* — Michael P Stafira
(74) *Attorney, Agent, or Firm* — Wilson Sonsini Goodrich & Rosati

(57) ABSTRACT

Methods and apparatus for measuring objects comprise a plurality of light sources to generate a plurality of light beams directed toward a spot generator array comprising a plurality of spot generating lenses. The plurality of light sources is separated from the spot generator array with a separation distance sufficient to overlap the plurality of light beams at each of the spot generating lenses. The overlap of each of the beams at each of the spot generating lenses provides smoothing of the energy profile of the light energy incident on the spot generating lenses. The spot generator array generates focused spots comprising overlapping focused beams. The overlapping beams may comprise overlapping beams of a vertical cavity surface emitting laser (VCSEL) array, and the overlapping focused beams can decrease optical artifacts.

16 Claims, 9 Drawing Sheets

(51) Int. Cl.
*G01B 11/24* (2006.01)
*F21V 5/04* (2006.01)
*G02B 27/09* (2006.01)
*G01B 11/06* (2006.01)
*A61C 9/00* (2006.01)

(52) U.S. Cl.
CPC .............. *G01B 11/24* (2013.01); *G01C 11/12* (2013.01); *G02B 27/0905* (2013.01); *G02B 27/0961* (2013.01); *A61C 9/0053* (2013.01)

(58) Field of Classification Search
CPC ....... G01N 21/553; G01N 2201/06113; G01N 2021/396; G01N 2021/399; G01N 21/39; G01N 21/49; G01N 21/6452; G01N 21/6454
See application file for complete search history.

(56) References Cited

U.S. PATENT DOCUMENTS

| | | |
|---|---|---|
| 3,600,808 A | 8/1971 | Reeve |
| 3,660,900 A | 5/1972 | Andrews |
| 3,683,502 A | 8/1972 | Wallshein |
| 3,738,005 A | 6/1973 | Cohen |
| 3,860,803 A | 1/1975 | Levine |
| 3,916,526 A | 11/1975 | Schudy |
| 3,922,786 A | 12/1975 | Lavin |
| 3,950,851 A | 4/1976 | Bergersen |
| 3,983,628 A | 10/1976 | Acevedo |
| 4,014,096 A | 3/1977 | Dellinger |
| 4,195,046 A | 3/1980 | Kesling |
| 4,253,828 A | 3/1981 | Coles et al. |
| 4,324,546 A | 4/1982 | Heitlinger et al. |
| 4,324,547 A | 4/1982 | Arcan et al. |
| 4,348,178 A | 9/1982 | Kurz |
| 4,478,580 A | 10/1984 | Barrut |
| 4,500,294 A | 2/1985 | Lewis |
| 4,504,225 A | 3/1985 | Yoshii |
| 4,505,673 A | 3/1985 | Yoshii |
| 4,526,540 A | 7/1985 | Dellinger |
| 4,575,330 A | 3/1986 | Hull |
| 4,575,805 A | 3/1986 | Moermann et al. |
| 4,591,341 A | 5/1986 | Andrews |
| 4,609,349 A | 9/1986 | Cain |
| 4,611,288 A | 9/1986 | Duret et al. |
| 4,656,860 A | 4/1987 | Orthuber et al. |
| 4,663,720 A | 5/1987 | Duret et al. |
| 4,664,626 A | 5/1987 | Kesling |
| 4,676,747 A | 6/1987 | Kesling |
| 4,742,464 A | 5/1988 | Duret et al. |
| 4,755,139 A | 7/1988 | Abbatte et al. |
| 4,763,791 A | 8/1988 | Halverson et al. |
| 4,793,803 A | 12/1988 | Martz |
| 4,798,534 A | 1/1989 | Breads |
| 4,836,778 A | 6/1989 | Baumrind et al. |
| 4,837,732 A | 6/1989 | Brandestini et al. |
| 4,850,864 A | 7/1989 | Diamond |
| 4,850,865 A | 7/1989 | Napolitano |
| 4,856,991 A | 8/1989 | Breads et al. |
| 4,877,398 A | 10/1989 | Kesling |
| 4,880,380 A | 11/1989 | Martz |
| 4,889,238 A | 12/1989 | Batchelor |
| 4,890,608 A | 1/1990 | Steer |
| 4,935,635 A | 6/1990 | O'Harra |
| 4,936,862 A | 6/1990 | Walker et al. |
| 4,937,928 A | 7/1990 | van der Zel |
| 4,941,826 A | 7/1990 | Loran et al. |
| 4,964,770 A | 10/1990 | Steinbichler et al. |
| 4,975,052 A | 12/1990 | Spencer et al. |
| 4,983,334 A | 1/1991 | Adell |
| 5,011,405 A | 4/1991 | Lemchen |
| 5,017,133 A | 5/1991 | Miura |
| 5,027,281 A | 6/1991 | Rekow et al. |
| 5,035,613 A | 7/1991 | Breads et al. |
| 5,055,039 A | 10/1991 | Abbatte et al. |
| 5,059,118 A | 10/1991 | Breads et al. |
| 5,100,316 A | 3/1992 | Wildman |
| 5,121,333 A | 6/1992 | Riley et al. |
| 5,125,832 A | 6/1992 | Kesling |
| 5,128,870 A | 7/1992 | Erdman et al. |
| 5,130,064 A | 7/1992 | Smalley |
| 5,131,843 A | 7/1992 | Hilgers et al. |
| 5,131,844 A | 7/1992 | Marinaccio et al. |
| 5,139,419 A | 8/1992 | Andreiko et al. |
| 5,145,364 A | 9/1992 | Martz et al. |
| 5,176,517 A | 1/1993 | Truax |
| 5,184,306 A | 2/1993 | Erdman et al. |
| 5,186,623 A | 2/1993 | Breads et al. |
| 5,257,203 A | 10/1993 | Riley et al. |
| 5,273,429 A | 12/1993 | Rekow et al. |
| 5,278,756 A | 1/1994 | Lemchen et al. |
| 5,328,362 A | 7/1994 | Watson et al. |
| 5,331,654 A | 7/1994 | Jewell et al. |
| 5,338,198 A | 8/1994 | Wu et al. |
| 5,340,309 A | 8/1994 | Robertson |
| 5,342,202 A | 8/1994 | Deshayes |
| 5,368,478 A | 11/1994 | Andreiko et al. |
| 5,372,502 A | 12/1994 | Massen et al. |
| 5,382,164 A | 1/1995 | Stern |
| 5,395,238 A | 3/1995 | Andreiko et al. |
| 5,412,680 A | 5/1995 | Swirhun et al. |
| 5,431,562 A | 7/1995 | Andreiko et al. |
| 5,440,326 A | 8/1995 | Quinn |
| 5,440,496 A | 8/1995 | Andersson et al. |
| 5,447,432 A | 9/1995 | Andreiko et al. |
| 5,452,219 A | 9/1995 | Dehoff et al. |
| 5,454,717 A | 10/1995 | Andreiko et al. |
| 5,456,600 A | 10/1995 | Andreiko et al. |
| 5,474,448 A | 12/1995 | Andreiko et al. |
| RE35,169 E | 3/1996 | Lemchen et al. |
| 5,518,397 A | 5/1996 | Andreiko et al. |
| 5,528,735 A | 6/1996 | Strasnick et al. |
| 5,533,895 A | 7/1996 | Andreiko et al. |
| 5,542,842 A | 8/1996 | Andreiko et al. |
| 5,549,476 A | 8/1996 | Stern |
| 5,562,448 A | 10/1996 | Mushabac |
| 5,587,912 A | 12/1996 | Andersson et al. |
| 5,605,459 A | 2/1997 | Kuroda et al. |
| 5,607,305 A | 3/1997 | Andersson et al. |
| 5,614,075 A | 3/1997 | Andre |
| 5,621,648 A | 4/1997 | Crump |
| 5,645,420 A | 7/1997 | Bergersen |
| 5,645,421 A | 7/1997 | Slootsky |
| 5,655,653 A | 8/1997 | Chester |
| 5,659,420 A * | 8/1997 | Wakai .................. G01B 11/026 356/511 |
| 5,683,243 A | 11/1997 | Andreiko et al. |
| 5,692,894 A | 12/1997 | Schwartz et al. |
| 5,725,376 A | 3/1998 | Poirier |
| 5,725,378 A | 3/1998 | Wang |
| 5,733,126 A | 3/1998 | Andersson et al. |
| 5,740,267 A | 4/1998 | Echerer et al. |
| 5,742,700 A | 4/1998 | Yoon et al. |
| 5,790,242 A | 8/1998 | Stern et al. |
| 5,799,100 A | 8/1998 | Clarke et al. |
| 5,800,174 A | 9/1998 | Andersson |
| 5,823,778 A | 10/1998 | Schmitt et al. |
| 5,848,115 A | 12/1998 | Little et al. |
| 5,857,853 A | 1/1999 | van Nifterick et al. |
| 5,866,058 A | 2/1999 | Batchelder et al. |
| 5,879,158 A | 3/1999 | Doyle et al. |
| 5,880,961 A | 3/1999 | Crump |
| 5,880,962 A | 3/1999 | Andersson et al. |
| 5,934,288 A | 8/1999 | Avila et al. |
| 5,957,686 A | 9/1999 | Anthony |
| 5,964,587 A | 10/1999 | Sato |
| 5,971,754 A | 10/1999 | Sondhi et al. |
| 5,975,893 A | 11/1999 | Chishti et al. |
| 6,015,289 A | 1/2000 | Andreiko et al. |
| 6,044,309 A | 3/2000 | Honda |
| 6,049,743 A | 4/2000 | Baba |
| 6,062,861 A | 5/2000 | Andersson |
| 6,068,482 A | 5/2000 | Snow |

(56) References Cited

U.S. PATENT DOCUMENTS

| | | | |
|---|---|---|---|
| 6,099,314 A | 8/2000 | Kopelman et al. | |
| 6,123,544 A | 9/2000 | Cleary | |
| 6,152,731 A | 11/2000 | Jordan et al. | |
| 6,183,248 B1 | 2/2001 | Chishti et al. | |
| 6,190,165 B1 | 2/2001 | Andreiko et al. | |
| 6,217,325 B1 | 4/2001 | Chishti et al. | |
| 6,217,334 B1 | 4/2001 | Hultgren | |
| 6,244,861 B1 | 6/2001 | Andreiko et al. | |
| 6,309,215 B1 | 10/2001 | Phan et al. | |
| 6,315,553 B1 | 11/2001 | Sachdeva et al. | |
| 6,322,359 B1 | 11/2001 | Jordan et al. | |
| 6,350,120 B1 | 2/2002 | Sachdeva et al. | |
| 6,382,975 B1 | 5/2002 | Poirier | |
| 6,398,548 B1 | 6/2002 | Muhammad et al. | |
| 6,402,707 B1 | 6/2002 | Ernst | |
| 6,482,298 B1 | 11/2002 | Bhatnagar | |
| 6,524,101 B1 | 2/2003 | Phan et al. | |
| 6,554,611 B2 | 4/2003 | Chishti et al. | |
| 6,572,372 B1 | 6/2003 | Phan et al. | |
| 6,573,998 B2 | 6/2003 | Cohen-Sabban | |
| 6,629,840 B2 | 10/2003 | Chishti et al. | |
| 6,705,863 B2 | 3/2004 | Phan et al. | |
| 6,722,880 B2 | 4/2004 | Chishti et al. | |
| 7,561,273 B2 | 7/2009 | Stautmeister et al. | |
| 7,626,705 B2 | 12/2009 | Altendorf | |
| 7,791,810 B2 | 9/2010 | Powell | |
| 8,126,025 B2 | 2/2012 | Takeda | |
| 8,451,456 B2 | 5/2013 | Babayoff | |
| 8,488,113 B2 | 7/2013 | Thiel et al. | |
| 8,577,212 B2 | 11/2013 | Thiel et al. | |
| 8,638,447 B2 | 1/2014 | Babayoff et al. | |
| 8,675,706 B2 | 3/2014 | Seurin et al. | |
| 8,743,923 B2 | 6/2014 | Geske et al. | |
| 8,767,270 B2 | 7/2014 | Curry et al. | |
| 9,261,358 B2* | 2/2016 | Atiya | G01B 11/25 |
| 2002/0006597 A1 | 1/2002 | Andreiko et al. | |
| 2003/0009252 A1 | 1/2003 | Pavlovskaia et al. | |
| 2003/0139834 A1 | 7/2003 | Nikolskiy et al. | |
| 2003/0224311 A1 | 12/2003 | Cronauer | |
| 2004/0128010 A1 | 7/2004 | Pavlovskaia et al. | |
| 2005/0055118 A1 | 3/2005 | Nikolskiy et al. | |
| 2007/0054280 A1* | 3/2007 | Li | C12Q 1/6837 435/6.11 |
| 2009/0218514 A1 | 9/2009 | Klunder et al. | |
| 2010/0008588 A1* | 1/2010 | Feldkhun | G01B 11/2518 382/206 |
| 2010/0046953 A1* | 2/2010 | Shaw | H01S 5/423 398/115 |
| 2011/0089315 A1* | 4/2011 | Walt | G02B 17/0615 250/251 |
| 2012/0081786 A1 | 4/2012 | Mizuyama et al. | |
| 2012/0147912 A1 | 6/2012 | Moench et al. | |
| 2012/0257387 A1 | 10/2012 | Kuchibhotla et al. | |
| 2012/0281293 A1 | 11/2012 | Gronenborn et al. | |
| 2013/0163627 A1 | 6/2013 | Seurin et al. | |
| 2013/0206967 A1 | 8/2013 | Shpunt et al. | |
| 2013/0266326 A1 | 10/2013 | Joseph et al. | |
| 2014/0023102 A1 | 1/2014 | Holder et al. | |
| 2014/0160488 A1* | 6/2014 | Zhou | G01B 9/02004 356/479 |

FOREIGN PATENT DOCUMENTS

| | | |
|---|---|---|
| AU | 5598894 A | 6/1994 |
| CA | 1121955 | 4/1982 |
| DE | 2749802 | 5/1978 |
| DE | 69327661 T | 7/2000 |
| EP | 0091876 A1 | 10/1983 |
| EP | 0299490 A2 | 1/1989 |
| EP | 0376873 A2 | 7/1990 |
| EP | 0490848 A2 | 6/1992 |
| EP | 0541500 A1 | 5/1993 |
| EP | 0667753 B1 | 8/1995 |
| EP | 0731673 B1 | 9/1996 |
| EP | 0774933 B1 | 5/1997 |
| EP | 1184706 A2 | 3/2002 |
| EP | 2772996 A2 | 9/2014 |
| ES | 463897 | 1/1980 |
| FR | 2369828 A1 | 6/1978 |
| FR | 2652256 A1 | 3/1991 |
| GB | 15500777 | 8/1979 |
| JP | 53-058191 | 5/1978 |
| JP | 04-028359 | 1/1992 |
| JP | 08-508174 | 9/1996 |
| JP | 2005-285697 A | 10/2005 |
| WO | WO 90/08512 A1 | 8/1990 |
| WO | WO 91/04713 A1 | 4/1991 |
| WO | WO 94/10935 A1 | 5/1994 |
| WO | WO 98/32394 A1 | 7/1998 |
| WO | WO 98/44865 A1 | 10/1998 |
| WO | WO 98/58596 A1 | 12/1998 |
| WO | WO 99/24786 A1 | 5/1999 |
| WO | WO 00/08415 A1 | 2/2000 |
| WO | WO 02/095475 A1 | 11/2002 |
| WO | WO 2007/090865 A1 | 8/2007 |
| WO | WO 2014/175901 A1 | 10/2014 |

OTHER PUBLICATIONS

U.S. Appl. No. 14/323,215, filed Jul. 3, 2014, Atiya et al.
U.S. Appl. No. 14/323,225, filed Jul. 3, 2014, Atiya et al.
U.S. Appl. No. 14/323,237, filed Jul. 3, 2014, Lampert et al.
U.S. Appl. No. 14/334,527, filed Jul. 17, 2014, Atiya et al.
CEREC Omnicam and CEREC Bluecam brochure. The first choice in every case. The Dental Company Sirona. 2014.
Dummer, et al. Computed Radiography Imaging Based on High-Density 670 nm VCSEL Arrays. Proceedings of SPIE vol. 7557, 75570H (2010)http://vixarinc.com/pdf/SPIE_radiography_manuscript_submission1.pdf.
Pellin Broca Prisms—Specifications. Thor Labs. Updated Nov. 30, 2012. www.thorlabs.com.
AADR. American Association for Dental Research, Summary of Activities, Mar. 20-23, 1980, Los Angeles, CA, p. 195.
Alcaniz, et al. "An Advanced System for the Simulation and Planning of Orthodontic Treatments," Karl HF Heinz Hohne and Ron Kikinis (eds.), Visualization in Biomedical Computing, 4th Intl. Conf., VBC '96, Hamburg, Germany, Sep. 22-25, 1996, Springer-Verlag, pp. 511-520.
Alexander et al., "The DigiGraph Work Station Part 2 Clinical Management," JCO, pp. 402-407 (Jul. 1990).
Altschuler et al., "Analysis of 3-D Data for Comparative 3-D Serial Growth Pattern Studies of Oral-Facial Structures," AADR Abstracts, Program and Abstracts of Papers, 57th General Session, IADR HP Annual Session, Mar. 29, 1979-Apr. 1, 1979, New Orleans Marriot, Journal of Dental Research, vol. 58, Jan. 1979, Special Issue A, p. 221.
Altschuler et al., "Laser Electro-Optic System for Rapid Three-Dimensional (3D) Topographic Mapping of Surfaces," Optical Engineering, 20(6):953-961 (1981).
Altschuler et al., "Measuring Surfaces Space-Coded by a Laser-Projected Dot Matrix," SPIE Imaging Applications for Automated Industrial Inspection and Assembly, vol. 182, p. 187-191 (1979).
Altschuler, "3D Mapping of Maxillo-Facial Prosthesis," AADR Abstract #607, 2 pages total, (1980).
Andersson et al., "Clinical Results with Titanium Crowns Fabricated with Machine Duplication and Spark Erosion," Acta. Odontol. Scand., 47:279-286 (1989).
Andrews, The Six Keys to Optimal Occlusion Straight Wire, Chapter 3, pp. 13-24 (1989).
Bartels, et al., An Introduction to Splines for Use in Computer Graphics and Geometric Modeling, Morgan Kaufmann Publishers, pp. 422-425 (1987).
Baumrind et al., "A Stereophotogrammetric System for the Detection of Prosthesis Loosening in Total Hip Arthroplasty," NATO Symposium on Applications of Human Biostereometrics, Jul. 9-13, 1978, SPIE, vol. 166, pp. 112-123.
Baumrind et al., "Mapping the Skull in 3-D," reprinted from J. Calif. Dent. Assoc., 48(2), 11 pages total, (1972 Fall Issue).

(56) References Cited

OTHER PUBLICATIONS

Baumrind, "A System for Craniofacial Mapping Through the Integration of Data from Stereo X-Ray Films and Stereo Photographs," an invited paper submitted to the 1975 American Society of Photogram Symposium on Close-Range Photogram Systems, University of Ill., Aug. 26-30, 1975, pp. 142-166.
Baumrind, "Integrated Three-Dimensional Craniofacial Mapping: Background, Principles, and Perspectives," Semin. in Orthod., 7(4):223-232 (Dec. 2001).
Begole et al., "A Computer System for the Analysis of Dental Casts," The Angle Orthod., 51(3):253-259 (Jul. 1981).
Bernard et al.,"Computerized Diagnosis in Orthodontics for Epidemiological Studies: A ProgressReport," Abstract, J. Dental Res. Special Issue, vol. 67, p. 169, paper presented at International Association for Dental Research 66th General Session, Mar. 9-13, 1988, Montreal, Canada.
Bhatia et al., "A Computer-Aided Design for Orthognathic Surgery," Br. J. Oral Maxillofac. Surg., 22:237-253 (1984).
Biggerstaff et al., "Computerized Analysis of Occlusion in the Postcanine Dentition," Am. J. Orthod., 61(3): 245-254 (Mar. 1972).
Biggerstaff, "Computerized Diagnostic Setups and Simulations," Angle Orthod., 40(1):28-36 (Jan. 1970).
Biostar Opeation & Training Manual. Great Lakes Orthodontics, Ltd. 199 Fire Tower Drive,Tonawanda, New York. 14150-5890, 20 pages total (1990).
Blu, et al., "Linear interpolation revitalized", IEEE Trans. Image Proc., 13(5):710-719 (May 2004).
Bourke, "Coordinate System Transformation," (Jun. 1996), p. 1, retrieved from the Internet Nov. 5, 2004, URL <http://astronomy.swin.edu.au/—pbourke/prolection/coords>.
Boyd et al., "Three Dimensional Diagnosis and Orthodontic Treatment of Complex Malocclusions With the Invisalipn Appliance," Semin. Orthod., 7(4):274-293 (Dec. 2001).
Brandestini et al., "Computer Machined Ceramic Inlays. In Vitro Marginal Adaptation," J. Dent. Res. Special Issue, Abstract 305, vol. 64, p. 208 (1985).
Brook et al., "An Image Analysis System for the Determination of Tooth Dimensions from Study Casts: Comparison with Manual Measurements of Mesio-distal Diameter," J. Dent. Res., 65(3):428-431 (Mar. 1986).
Burstone (interview), "Dr. Charles J. Burstone on the Uses of the Computer in Orthodontic Practice (Part 1)," J. Clin. Orthod., 13(7):442-453 (Jul. 1979).
Burstone (interview), "Dr. Charles J. Burstone on the Uses of the Computer in Orthodontic Practice (Part 2)," J. Clin. Orthod., 13(8):539-551 (Aug. 1979).
Burstone et al., Precision Adjustment of the Transpalatal Lingual Arch: Computer Arch Form Predetermination, Am, Journal of Orthodontics, vol. 79, No. 2 (Feb. 1981), pp. 115-133.
Cardinal Industrial Finishes, Powder Coatings information posted at <http://www.cardinalpaint.com> on Aug. 25, 2000, 2 pages.
Carnaghan, "An Alternative to Holograms for the Portrayal of Human Teeth," 4th Int'l. Conf. on Holographic Systems, Components and Applications, Sep. 15, 1993, pp. 228-231.
Chaconas et al., "The DigiGraph Work Station, Part 1, Basic Concepts," JCO, pp. 360-367 (Jun. 1990).
Chafetz et al., "Subsidence of the Femoral Prosthesis, A Stereophotogrammetric Evaluation," Clin. Orthop. Relat. Res., No. 201, pp. 60-67 (Dec. 1985).
Chiappone, (1980). Constructing the Gnathologic Setup and Positioner, J. Clin. Orthod, vol. 14, pp. 121-133.
Cottingham, (1969). Gnathologic Clear Plastic Positioner, Am. J. Orthod, vol. 55, pp. 23-31.
Crawford, "CAD/CAM in the Dental Office: Does It Work?", Canadian Dental Journal, vol. 57, No. 2, pp. 121-123 (Feb. 1991).
Crawford, "Computers in Dentistry: Part 1: CAD/CAM: The Computer Moves Chairside," "Part 2: F. Duret—A Man With a Vision," "Part 3: The Computer Gives New Vision—Literally," "Part 4: Bytes 'N Bites" The Computer Moves From the Front Desk to the Operatory, Canadian Dental Journal, vol. 54(9), pp. 661-666 (1988).

Crooks, "CAD/CAM Comes to USC," USC Dentistry, pp. 14-17 (Spring 1990).
Cureton, Correcting Malaligned Mandibular Incisors with Removable Retainers, J. Clin. Orthod, vol. 30, No. 7 (1996) pp. 390-395.
Curry et al., "Integrated Three-Dimensional Craniofacial Mapping at the Craniofacial Research Instrumentation Laboratory/University of the Pacific," Semin Orthod., 7(4):258-265 (Dec. 2001).
Cutting et al., "Three-Dimensional Computer-Assisted Design of Craniofacial Surgical Procedures: Optimization and Interaction with Cephalometric and CT-Based Models," Plast. 77(6):877-885 (Jun. 1986).
DCS Dental AG, "The CAD/CAM 'DCS Titan System' for Production of Crowns/Bridges," DSC Production, pp. 1-7 (Jan. 1992).
Definition for gingiva. Dictionary.com p. 1-3. Retrieved from the internet Nov. 5, 2004 <http://reference.com/search/search?q=gingiva>.
Defranco et al., "Three-Dimensional Large Displacement Analysis of Orthodontic Appliances," J. Biomechanics, 9:793-801 (1976).
Dental Institute University of Zurich Switzerland, Program for International Symposium on Computer Restorations: State of the Art of the CEREC-Method, May 1991, 2 pages total.
Dentrac Corporation, Dentrac document, pp. 4-13 (1992).
Dent-X posted on Sep. 24, 1998 at <http://www.dent-x.com/DentSim.htm>, 6 pages.
Doyle, "Digital Dentistry," Computer Graphics World, pp. 50-52, 54 (Oct. 2000).
DuraClearTM product information, Allesee Orthodontic Appliances-Pro Lab, 1 page (1997).
Duret et al, "CAD-CAM in Dentistry," J. Am. Dent. Assoc. 117:715-720 (Nov. 1988).
Duret et al., "CAD/CAM Imaging in Dentistry," Curr. Opin. Dent., 1:150-154 (1991).
Duret, "The Dental CAD/CAM, General Description of the Project," Hennson International Product Brochure, 18 pages total, Jan. 1986.
Duret,"Vers Une Prosthese Informatisee," (English translation attached), Tonus, vol. 75, pp. 55-57 (Nov. 15, 1985).
Economides, "The Microcomputer in the Orthodontic Office," JCO, pp. 767-772 (Nov. 1979).
Elsasser, Some Observations on the History and Uses of the Kesling Positioner, Am. J. Orthod. (1950) 36:368-374.
English translation of Japanese Laid-Open Publication No. 63-11148 to inventor T. Ozukuri (Laid-Open on Jan. 18, 1998) pp. 1-7.
Faber et al., "Computerized Interactive Orthodontic Treatment Planning," Am. J. Orthod., 73(1):36-46 (Jan. 1978).
Felton et al., "A Computerized Analysis of the Shape and Stability of Mandibular Arch Form," Am. J. Orthod. Dentofacial Orthop., 92(6):478-483 (Dec. 1987).
Friede et al., "Accuracy of Cephalometric Prediction in Orthognathic Surgery," Abstract of Papers, J. Dent. Res., 70:754-760 (1987).
Futterling et al., "Automated Finite Element Modeling of a Human Mandible with Dental Implants," JS WSCG '98—Conference Program, retrieved from the Internet: <http://wscg.zcu.cz/wscg98/papers98/Strasser 98.pdf>, 8 pages.
Gao et al., "3-D element Generation for Multi-Connected Complex Dental and Mandibular Structure," Proc. Intl Workshop on Medical Imaging and Augmented Reality, pp. 267-271 (Jun. 12, 2001).
Gim-Alldent Deutschland, "Das DUX System: Die Technik," 2 pages total (2002).
Gottleib et al., "JCO Interviews Dr. James A. McNamura, Jr., on the Frankel Appliance: Part 2: Clinical 1-1 Management,"J. Clin. Orthod., 16(6):390-407 (Jun. 1982).
Grayson, "New Methods for Three Dimensional Analysis of Craniofacial Deformity, Symposium: Computerized Facial Imaging in Oral and Maxiiofacial Surgery," AAOMS, 3 pages total, (Sep. 13, 1990).
Guess et al., "Computer Treatment Estimates in Orthodontics and Orthognathic Surgery," JCO, pp. 262-28 (Apr. 1989).
Heaven et al., "Computer-Based Image Analysis of Artificial Root Surface Caries," Abstracts of Papers, J. Dent. Res., 70:528 (Apr. 17-21, 1991).

(56) References Cited

OTHER PUBLICATIONS

Highbeam Research, "Simulating Stress Put on Jaw," Tooling & Production [online], Nov. 1996, n pp. 1-2, retrieved from the Internet on Nov. 5, 2004, URL http://static.highbeam.com/t/toolingampproduction/november011996/simulatingstressp-utonfa . . . >.
Hikage, "Integrated Orthodontic Management System for Virtual Three-Dimensional Computer Graphic Simulation and Optical Video Image Database for Diagnosis and Treatment Planning", Journal of Japan Orthodontic Society, Feb. 1987, English translation, pp. 1-38, Japanese version, 46(2), pp. 248-269 (60 pages total).
Hoffmann, et al., "Role of Cephalometry for Planning of Jaw Orthopedics and Jaw Surgery Procedures," (Article Summary in English, article in German), lnformatbnen, pp. 375-396 (Mar. 1991).
Hojjatie et al., "Three-Dimensional Finite Element Analysis of Glass-Ceramic Dental Crowns," J. Biomech., 23(11):1157-1166 (1990).
Huckins, "CAD-CAM Generated Mandibular Model Prototype from MRI Data," AAOMS, p. 96 (1999).
Important Tip About Wearing the Red White & Blue Active Clear Retainer System, Allesee Orthodontic Appliances-Pro Lab, 1 page 1998).
JCO Interviews, Craig Andreiko , DDS, MS on the Elan and Orthos Systems, JCO, pp. 459-468 (Aug. 1994).
JCO Interviews, Dr. Homer W. Phillips on Computers in Orthodontic Practice, Part 2, JCO. 1997; 1983:819-831.
Jerrold, "The Problem, Electronic Data Transmission and the Law," AJO-DO, pp. 478-479 (Apr. 1988).
Jones et al., "An Assessment of the Fit of a Parabolic Curve to Pre- and Post-Treatment Dental Arches," Br. J. Orthod., 16:85-93 (1989).
Kamada et.al., Case Reports on Tooth Positioners Using LTV Vinyl Silicone Rubber, J. Nihon University School of Dentistry (1984) 26(1): 11-29.
Kamada et.al., Construction of Tooth Positioners with LTV Vinyl Silicone Rubber and Some Case KJ Reports, J. Nihon University School of Dentistry (1982) 24(1):1-27.
Kanazawa et al., "Three-Dimensional Measurements of the Occlusal Surfaces of Upper Molars in a Dutch Population," J. Dent Res., 63(11):1298-1301 (Nov. 1984).
Kesling et al., The Philosophy of the Tooth Positioning Appliance, American Journal of Orthodontics and Oral surgery. 1945; 31:297-304.
Kesling, Coordinating the Predetermined Pattern and Tooth Positioner with Conventional Treatment, Am. J. Orthod. Oral Surg. (1946) 32:285-293.
Kleeman et al., The Speed Positioner, J. Clin. Orthod. (1996) 30:673-680.
Kochanek, "Interpolating Splines with Local Tension, Continuity and Bias Control," Computer Graphics, ri 18(3):33-41 (Jul. 1984). KM Oral Surgery (1945) 31 :297-30.
Kunii et al., "Articulation Simulation for an Intelligent Dental Care System," Displays 15:181-188 (1994).
Kuroda et al., Three-Dimensional Dental Cast Analyzing System Using Laser Scanning, Am. J. Orthod. Dentofac. Orthop. (1996) 110:365-369.
Laurendeau, et al., "A Computer-Vision Technique for the Acquisition and Processing of 3-D Profiles of 7 Dental Imprints: An Application in Orthodontics," IEEE Transactions on Medical Imaging, 10(3):453-461 (Sep. 1991).
Leinfelder, et al., "A New Method for Generating Ceramic Restorations: a CAD-CAM System," J. Am. 1-1 Dent. Assoc., 118(6):703-707 (Jun. 1989).
Manetti, et al., "Computer-Aided Cefalometry and New Mechanics in Orthodontics," (Article Summary in English, article in German), Fortschr Kieferorthop. 44, 370-376 (Nr. 5), 1983.
McCann, "Inside the ADA," J. Amer. Dent. Assoc., 118:286-294 (Mar. 1989).
McNamara et al., "Invisible Retainers," J. Cfin. Orthod., pp. 570-578 (Aug. 1985).
McNamara et al., Orthodontic and Orthopedic Treatment in the Mixed Dentition, Needham Press, pp. 347-353 (Jan. 1993).
Moermann et al., "Computer Machined Adhesive Porcelain Inlays: Margin Adaptation after Fatigue Stress," IADR Abstract 339, J. Dent. Res., 66(a):763 (1987).
Moles, "Correcting Mild Malalignments—As Easy as One, Two, Three," AOA/Pro Corner, vol. 11, No. 1, 2 pages (2002).
Mormann et al., "Marginale Adaptation von adhasuven Porzellaninlays in vitro," Separatdruck aus:Schweiz. Mschr. Zahnmed. 95: 1118-1129, 1985.
Nahoum, "The Vacuum Formed Dental Contour Appliance," N. Y. State Dent. J., 30(9):385-390 (Nov. 1964).
Nash, "CEREC CAD/CAM Inlays: Aesthetics and Durability in a Single Appointment," Dent. Today, 9(8):20, Oct. 22-23, 1990.
Nishiyama et al., "A New Construction of Tooth Repositioner by LTV Vinyl Silicone Rubber," J. Nihon Univ. Sch. Dent., 19(2):93-102 (1977).
Paul et al., "Digital Documentation of Individual Human Jaw and Tooth Forms for Applications in Orthodontics, Oral Surgery and Forensic Medicine" Proc. of the 24th Annual Conf. of the IEEE Industrial Electronics Society (IECON '98), Sep. 4, 1998, pp. 2415-2418.
Pinkham, "Foolish Concept Propels Technology," Dentist, 3 pages total, Jan./Feb. 1989.
Pinkham, "Inventor's CAD/CAM May Transform Dentistry," Dentist, 3 pages total, Sep. 1990.
Ponitz, "Invisible Retainers," Am. J. Orthod., 59(3):266-272 (Mar. 1971).
PROCERA Research Projects, "PROCERA Research Projects 1993—Abstract Collection," pp. 3-7, 28 (1993).
Proffit et al., Contemporary Orthodontics, (Second Ed.), Chapter 15, Mosby Inc., pp. 470-533 (Oct. 1993).
Raintree Essix & ARS Materials, Inc., Raintree Essix, Technical Magazine Table of contents and Essix Appliances, <http://www.essix.com/magazine/defaulthtml> Aug. 13, 1997.
Redmond et al., "Clinical Implications of Digital Orthodontics," Am. J. Orthod. Dentofacial Orthop., 117(2):240-242 (2000).
Rekow et al., "CAD/CAM for Dental Restorations—Some of the Curious Challenges," IEEE Trans. Biomed. Eng., 38(4):314-318 (Apr. 1991).
Rekow et al., "Comparison of Three Data Acquisition Techniques for 3-D Tooth Surface Mapping," Annual International Conference of the IEEE Engineering in Medicine and Biology Society, 13(1):344-345 1991.
Rekow, "A Review of the Developments in Dental CAD/CAM Systems," (contains references to Japanese efforts and content of the papers of particular interest to the clinician are indicated with a one line summary of their content in the bibliography), Curr. Opin. Dent., 2:25-33 (Jun. 1992).
Rekow, "CAD/CAM in Dentistry: A Historical Perspective and View of the Future," J. Can. Dent. Assoc., 58(4):283, 287-288 (Apr. 1992).
Rekow, "Computer-Aided Design and Manufacturing in Dentistry: A Review of the State of the Art," J. Prosthet. Dent., 58(4):512-516 (Oct. 1987).
Rekow, "Dental CAD-CAM Systems: What is the State of the Art?", J. Amer. Dent. Assoc., 122:43-48 1991.
Rekow, "Feasibility of an Automated System for Production of Dental Restorations, Ph.D. Thesis," Univ. of Minnesota, 244 pages total, Nov. 1988.
Richmond et al., "The Development of a 3D Cast Analysis System," Br. J. Orthod., 13(1):53-54 (Jan. 1986).
Richmond et al., "The Development of the PAR Index (Peer Assessment Rating): Reliability and Validity," Eur. J. Orthod., 14:125-139 (1992).
Richmond, "Recording the Dental Cast in Three Dimensions," Am. J. Orthod. Dentofacial Orthop., 92(3):199-206 (Sep. 1987).
Rudge, "Dental Arch Analysis: Arch Form, A Review of the Literature," Eur. J. Orthod., 3(4):279-284 1981.
Sakuda et al., "Integrated Information-Processing System in Clinical Orthodontics: An Approach with Use of a Computer Network System," Am. J. Orthod. Dentofacial Orthop., 101(3): 210-220 (Mar. 1992).

(56) References Cited

OTHER PUBLICATIONS

Schellhas et al., "Three-Dimensional Computed Tomography in Maxillofacial Surgical Planning," Arch. Otolamp!. Head Neck Surg., 114:438-442 (Apr. 1988).
Schroeder et al., Eds. The Visual Toolkit, Prentice Hall PTR, New Jersey (1998) Chapters 6, 8 & 9, (pp. 153-210,309-354, and 355-428, respectively).
Shilliday, (1971). Minimizing finishing problems with the mini-positioner, Am. J. Orthod. 59:596-599.
Siemens, "CEREC—Computer-Reconstruction," High Tech in der Zahnmedizin, 14 pages total (2004).
Sinclair, "The Readers' Corner," J. Clin. Orthod., 26(6):369-372 (Jun. 1992).
Sirona Dental Systems GmbH, CEREC 3D, Manuel utiiisateur, Version 2.0X (in French), 2003,114 pages total.
Stoll et al., "Computer-aided Technologies in Dentistry," (article summary in English, article in German), Dtsch Zahna'rztl Z 45, pp. 314-322 (1990).
Sturman, "Interactive Keyframe Animation of 3-D Articulated Models," Proceedings Graphics Interface '84, May-Jun. 1984, pp. 35-40.
The Choice Is Clear: Red, White & Blue . . . The Simple, Affordable, No-Braces Treatment, Allesee Orthodontic Appliances—Pro Lab product information for doctors. http://ormco.com/aoa/appliances-services/RWB/doctorhtml>, 5 pages (May 19, 2003).
The Choice is Clear: Red, White & Blue . . . The Simple, Affordable, No-Braces Treatment, Allesee Orthodontic Appliances—Pro Lab product information for patients, <http://ormco.com/aoa/appliancesservices/RWB/patients.html>, 2 pages (May 19, 2003).
The Choice Is Clear: Red, White & Blue . . . The Simple, Affordable, No-Braces Treatment, Allesee Orthodontic Appliances—Pro Lab product information, 6 pages (2003).
The Red, White & Blue Way to Improve Your Smile! Allesee Orthodontic Appliances—Pro Lab product information for patients, 2 pages 1992.
Truax L., "Truax Clasp-Less(TM) Appliance System," Funct. Orthod., 9(5):22-4, 26-8 (Sep.-Oct. 1992).
Tru-Tain Orthodontic & Dental Supplies, Product Brochure, Rochester, Minnesota 55902, 16 pages total (1996).
U.S. Department of Commerce, National Technical Information Service, "Automated Crown Replication Using Solid Photography SM," Solid Photography Inc., Melville NY, Oct. 1977, 20 pages total.
U.S. Department of Commerce, National Technical Information Service, "Holodontography: An Introduction to Dental Laser Holography," School of Aerospace Medicine Brooks AFB Tex, Mar. 1973, 37 pages total.
U.S. Appl. No. 60/050,342, filed on Jun. 20, 1997, 41 pages total.
Van Der Linden et al., "Three-Dimensional Analysis of Dental Casts by Means of the Optocom," J. Dent. Res., p. 1100 (Jul.-Aug. 1972).
Van Der Linden, "A New Method to Determine Tooth Positions and Dental Arch Dimensions," J. Dent. Res., 51(4):1104 (Jul.-Aug. 1972).
Van Der Zel, "Ceramic-Fused-to-Metal Restorations with a New CAD/CAM System," Quintessence Int., 24(11):769-778 (1993).
Varady et al., "Reverse Engineering of Geometric Models—An Introduction," Computer-Aided Design, 29(4):255-268,1997.
Verstreken et al., "An Image-Guided Planning System for Endosseous Oral Implants," IEEE Trans. Med. Imaging, 17(5):842-852 (Oct. 1998).
Warunek et al., Physical and Mechanical Properties of Elastomers in Orthodonic Positioners, Am J. Orthod. Dentofac. Orthop, vol. 95, No. 5, (May 1989) pp. 399-400.
Warunek et.al., Clinical Use of Silicone Elastomer Applicances, JCO (1989) XXIII(10):694-700.
Wells, Application of the Positioner Appliance in Orthodontic Treatment, Am. J. Orthodont. (1970) 58:351-366.
Williams, "Dentistry and CAD/CAM: Another French Revolution," J. Dent. Practice Admin., pp. 2-5 (Jan./Mar. 1987).
Williams, "The Switzerland and Minnesota Developments in CAD/CAM," J. Dent. Practice Admin., pp. 50-55 (Apr./Jun. 1987).
Wishan, "New Advances in Personal Computer Applications for Cephalometric Analysis, Growth Prediction, Surgical Treatment Planning and Imaging Processing," Symposium: Computerized Facial Imaging in Oral and Maxilofacial Surgery Presented on Sep. 13, 1990.
WSCG'98—Conference Program, "The Sixth International Conference in Central Europe on Computer Graphics and Visualization '98," Feb. 9-13, 1998, pp. 1-7, retrieved from the Internet on Nov. 5, 2004, URL<http://wscg.zcu.cz/wscg98/wscg98.h>.
Xia et al., "Three-Dimensional Virtual-Reality Surgical Planning and Soft-Tissue Prediction for Orthognathic Surgery," IEEE Trans. Inf. Technol. Biomed., 5(2):97-107 (Jun. 2001).
Yamamoto et al., "Optical Measurement of Dental Cast Profile and Application to Analysis of Three-Dimensional Tooth Movement in Orthodontics," Front. Med. Biol. Eng., 1(2):119-130 (1988).
Yamamoto et al., "Three-Dimensional Measurement of Dental Cast Profiles and Its Applications to Orthodontics," Conf. Proc. IEEE Eng. Med. Biol. Soc., 12(5):2051-2053 (1990).
Yamany et al., "A System for Human Jaw Modeling Using Intra-Oral Images," Proc. of the 20th Annual Conf. of the IEEE Engineering in Medicine and Biology Society, Nov. 1, 1998, vol. 2, pp. 563-566.
Yoshii, "Research on a New Orthodontic Appliance: The Dynamic Positioner (D.P.); I. The D.P. Concept and Implementation of Transparent Silicone Resin (Orthocon)," Nippon Dental Review, 452:61-74 (Jun. 1980).
Yoshii, "Research on a New Orthodontic Appliance: The Dynamic Positioner (D.P.); II. The D.P. Manufacturing Procedure and Clinical Applications," Nippon Dental Review, 454:107-130 (Aug. 1980).
Yoshii, "Research on a New Orthodontic Appliance: The Dynamic Positioner (D.P.); III.—The General Concept of the D.P. Method and Its Therapeutic Effect, Part 2. Skeletal Reversed Occlusion Case Reports," Nippon Dental Review, 458:112-129 (Dec. 1980).
Yoshii, "Research on a New Orthodontic Appliance: The Dynamic Positioner (D.P.); III. The General Concept of the D.P. Method and Its Therapeutic Effect, Part 1, Dental and Functional Reversed Occlusion Case Reports," Nippon Dental Review, 457:146-164 (Nov. 1980).
You May Be a Candidate for This Invisible No-Braces Treatment, Allesee Orthodontic Appliances—Pro Lab product information for patients, 2 pages (2002).

* cited by examiner

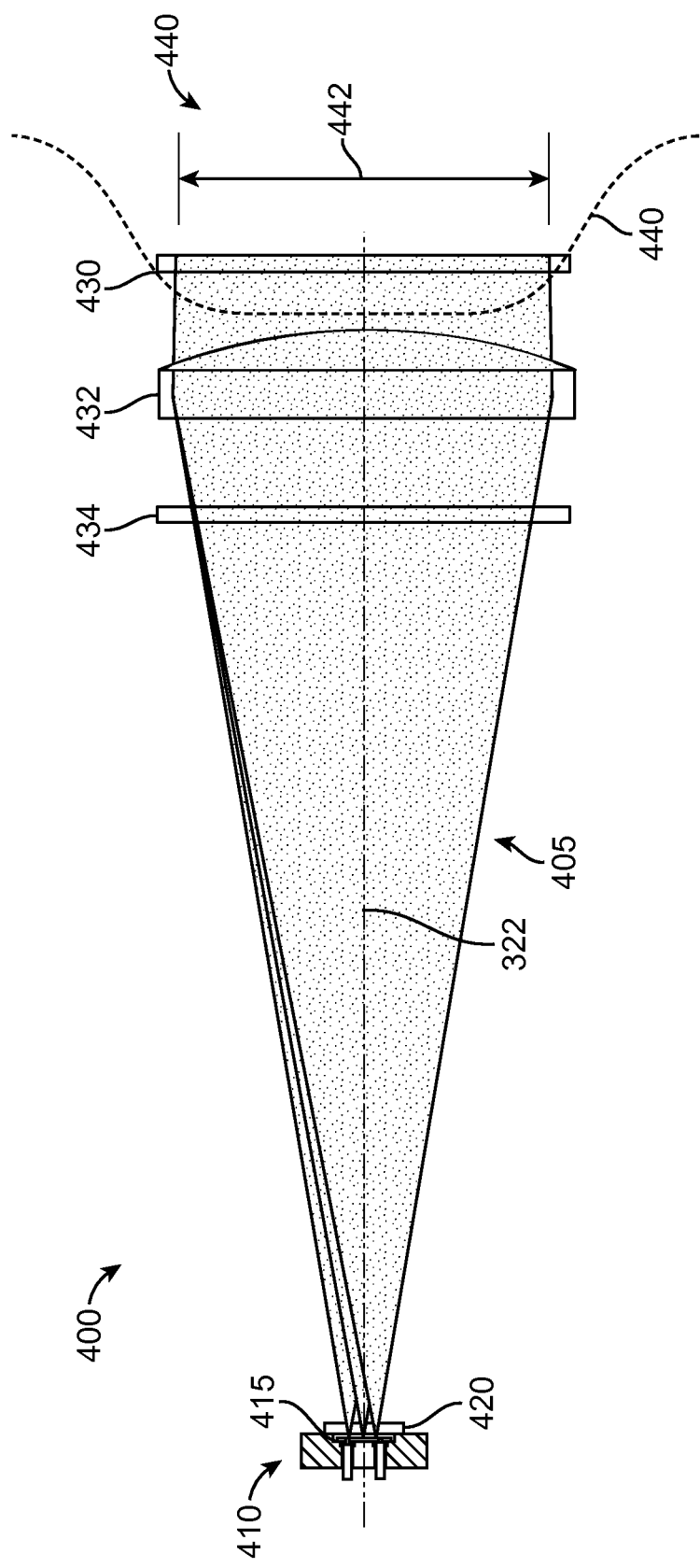

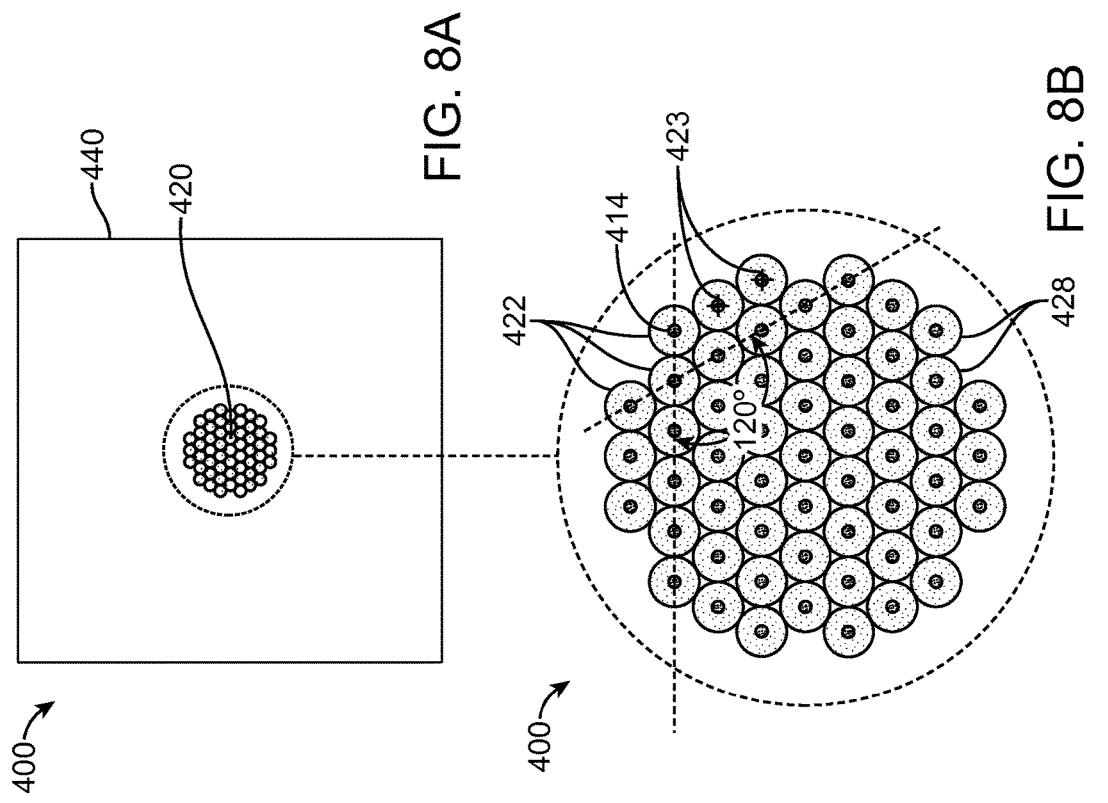
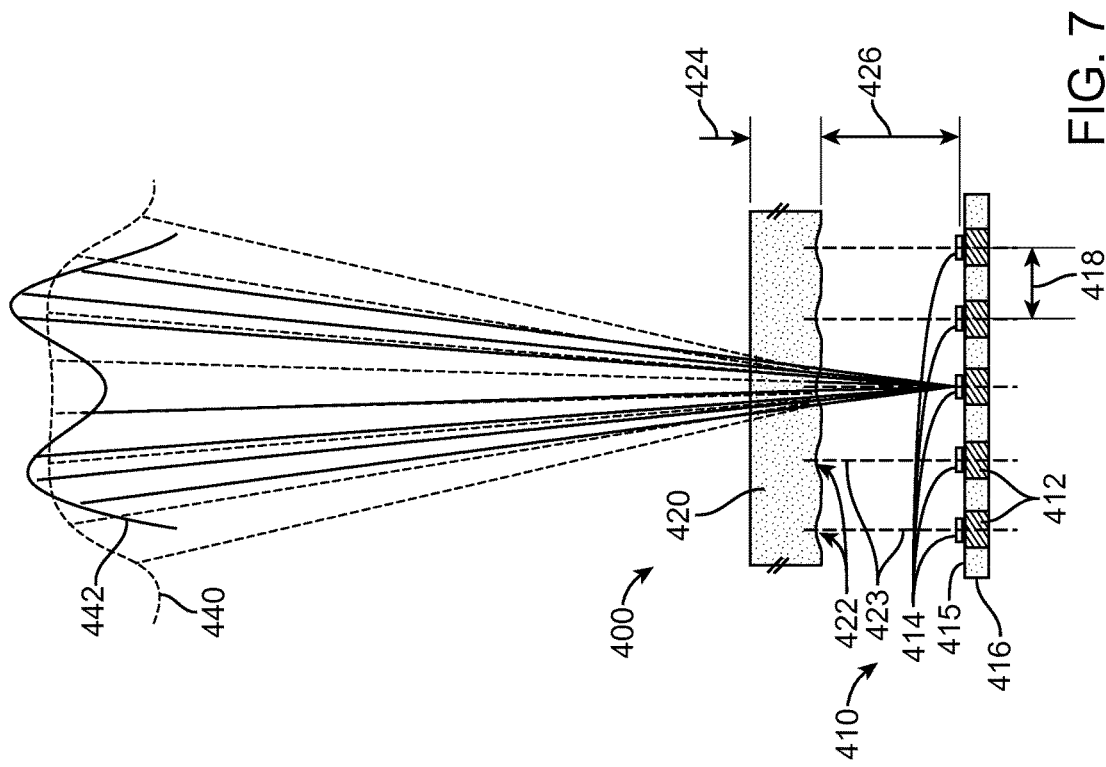

VCSEL BASED LOW COHERENCE EMITTER FOR CONFOCAL 3D SCANNER

BACKGROUND

The present invention is related to the measurement of objects. Although specific reference is made to intraoral scanning of teeth, embodiments as disclosed herein will find application in many fields such as topography and wavefront measurements.

Many dental and orthodontic procedures can benefit from accurate three-dimensional (3D) topographical measurements of a patient's intraoral cavity. For example, in the design and fabrication of dental prostheses (e.g., crowns or bridges), 3D models of the prosthesis site and surrounding dentition are typically used to ensure proper fit of the prosthesis. In many orthodontic procedures, 3D models of the patient's dental arches are utilized to design orthodontic appliances and develop treatment plans (e.g., to correct malocclusions). Various approaches can be used to produce such 3D models. For example, a physical model can be constructed from an impression of the patient's dentition. Alternatively, the intraoral cavity can be scanned to provide a virtual model suitable for use within computer-assisted design and computer-assisted manufacture (CAD/CAM) methods as well as digital treatment planning.

Scanning of the intraoral cavity may be performed by a dental or orthodontic practitioner. Previous methods and systems for scanning the intraoral cavity, however, can be less than ideal with regards to the accuracy and size of the scanning probe that is used to measure the teeth of the patient. Work in relation to embodiments suggests that the formation of light spots with such prior scanning systems can be less than ideal and may be related to measurement noise and less than ideal measurements in at least some instances. The focused spots may comprise artifacts related to the light source such as speckle, and these artifacts can affect measurement accuracy. Also, the size of the hand held probe that is positioned to measure the teeth can be somewhat larger and more difficult to position than would be ideal in at least some instances.

In light of the above, there is a need for improved methods and systems for scanning an intraoral cavity of a patient. Ideally, such systems would be more accurate and easier to manipulate than the prior scanning devices.

SUMMARY

Embodiments provide improved methods and apparatus for measuring objects. In many embodiments, a plurality of light sources generates a plurality of light beams directed toward a spot generator array comprising a plurality of spot generating lenses. The plurality of light sources is separated from the spot generator array with a separation distance sufficient to overlap the plurality of light beams at each of the spot generating lenses. The overlap of each of the beams at each of the spot generating lenses provides smoothing of the energy profile of the light energy incident on the spot generating lenses. Each of the spot generating lenses focuses the overlapping light beams to a focused spot. The focused spot of each spot generating lens comprises focused spots of a segment of the overlapping beams. In many embodiments, the focused spots of each of the overlapping beams overlap each other with sufficient overlap such that the individual focused spots of each of the beams cannot be discerned from other focused spots of the overlapping beams. The focused spots comprising the overlapping focused beams can provide decreased noise when combined with an optical measurement system such as an intraoral scanner. The overlapping beams may comprise overlapping beams of a laser diode array such as a vertical cavity surface emitting laser (VCSEL) array, and the overlapping focused beams can decrease optical artifacts of the focused spot defined with the plurality of beams. In many embodiments, each of the plurality of laser sources are not coherent with each other in order to smooth each focused spot with the plurality of focused beams.

In many embodiments, the light sources are spaced from adjacent light sources with a spacing distance and the spot generator lenses comprise a focal length. The separation distance, the spacing distance and the focal length can be arranged to provide the overlapping focused beams such that the individual focused spots of each of the beams cannot be discerned from other focused spots of the overlapping beams. This arrangement of the separation distance, the spacing distance and the focal length can be well suited for use with a laser diode array such as a vertical cavity surface emitting laser (VCSEL) array with decreased noise and coherence artifacts of generated spots.

In many embodiments, a homogenizing lens array comprising a plurality of homogenizing lenses can be located between the plurality of light sources and the spot generator array. Each lens of the homogenizing lens array can be registered with a corresponding light source such that the far field light profile from the corresponding light source is homogenized with the corresponding lens in registration with the light source. Each lens of the homogenizing array provides a substantially uniform intensity profile such as a top hat profile at the spot generator. The uniform intensity profile has the advantage of providing similar amounts of energy to each lens of the spot generator. In many embodiments, the lenses of the homogenizing array are configured to provide a homogenized far field pattern at the spot generator array. The lenses of the homogenizing array may comprise one or more of refractive optics, diffractive optics, or holographic optics to provide the homogenized beam profile for each light source. The substantially uniform beam energy profile for each light source can overlap with the substantially uniform beam energy profile with other light sources in order to provide increased uniformity to the energy profile at the spot generator and decreased coherence artifact of the focused spots.

INCORPORATION BY REFERENCE

All publications, patents, and patent applications mentioned in this specification are herein incorporated by reference in their entirety to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 6 shows components of a spot generator as in FIG. 5;

FIG. 7 shows a side view of a VCSEL array and microlens array to produce a homogenized far field energy distribution profile, in accordance with many embodiments;

FIG. 8A shows top view of the VCSEL array and microlens array of FIG. 7;

FIG. 8B shows an enlarged top view of the VCSEL array and microlens array of FIGS. 7 and 8A.

DETAILED DESCRIPTION

Figure 1A:
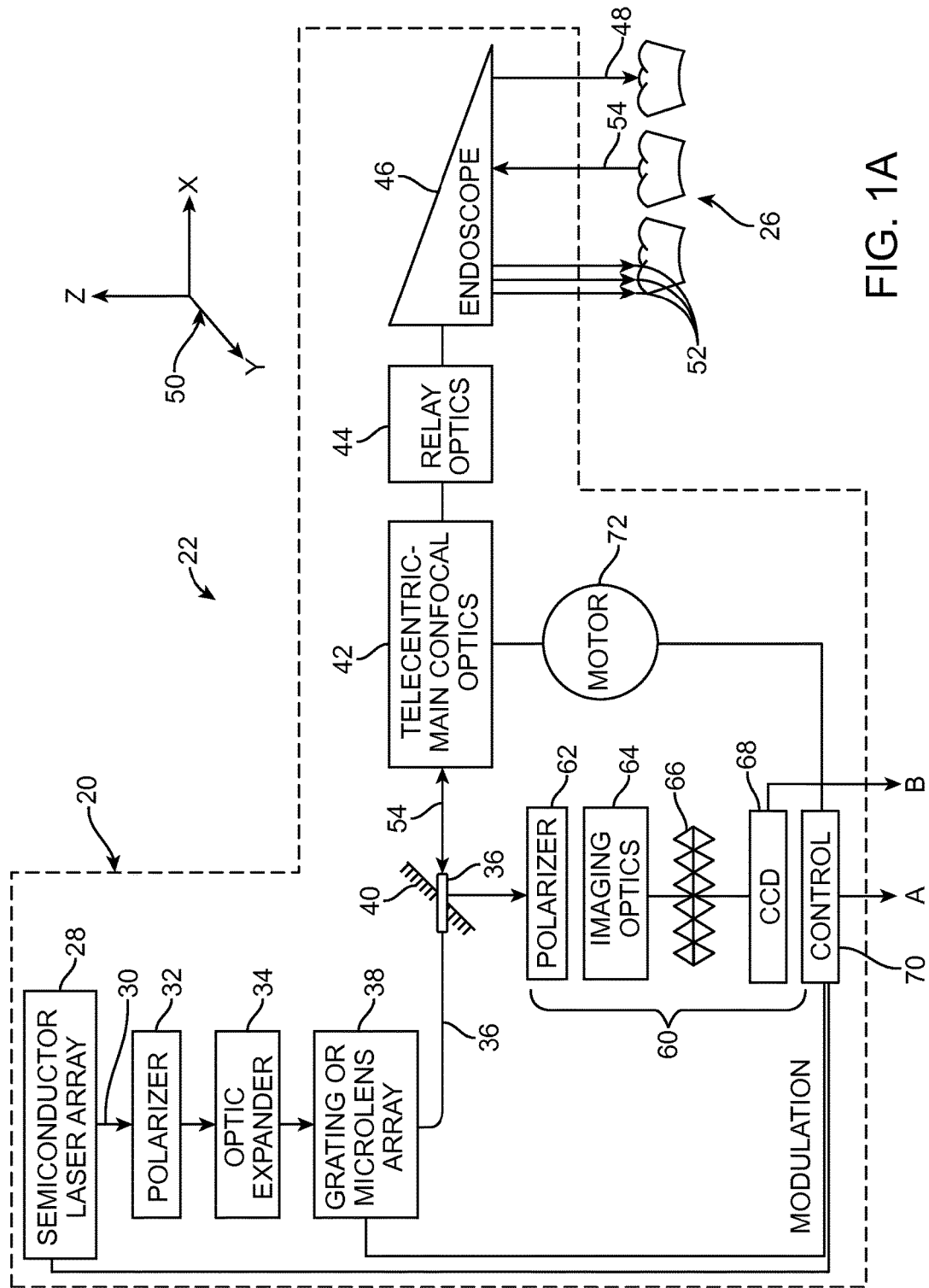
FIGS. 1A and 1B schematically illustrate, by way of a block diagram, an apparatus in accordance with many embodiments (FIG. 1B is a continuation of FIG. 1A)

Methods and systems described herein provide visual guidance for a user (e.g., a dental or orthodontic practitioner) during an intraoral scanning procedure. The method and systems described herein can be combined in many ways and are well suited for combination for intraoral scanners used for measuring portions of the intraoral cavity, for example. Embodiments as described herein can be combined with one or more components of prior scanning devices. In at least some embodiments, the single point source laser of the prior scanners can be replaced with an array of vertical cavity surface emitting lasers ("VCSELs") and appropriate optics provided and configured in order to incorporate the VCSEL array.

Any of the embodiments provided herein can be combined with other embodiments to the extent that such embodiments are not inconsistent with the teachings described herein.

As used herein A and/or B encompasses A alone, B alone, and combinations of A and B.

As used herein light encompasses one or more of visible light, ultraviolet light or infrared light.

As used herein a microlens encompasses a lens having dimensions measurable in micrometers, which can be a millimeter or more.

In many embodiments, an apparatus to measure an object comprises a plurality of light sources and a plurality of spot generating lenses. The plurality of light sources can be arranged to generate a plurality of light beams. The plurality of spot generating lenses can be configured to focus the plurality of beams to a plurality of focused spots, in which each of the plurality of focused spots comprises a focused portion of each of the plurality of light beams. The focused portion of each of the plurality of beams may overlap with other focused portions of other beams in order to define said each of the plurality of focused spots and inhibit noise.

In many embodiments, the apparatus comprises a scanning confocal apparatus to measure topography of the object in response to scanning of each of the plurality of focused spots.

In many embodiments, the plurality of spot generating lenses is separated from the plurality of light sources with a separation distance, and each of the plurality of lenses comprising a focal length, and each of the plurality of light sources comprising a spacing distance from adjacent sources of the plurality of light sources. The separation distance, the focal length and the spacing distance can be arranged to overlap the focused portion of each of the plurality of beams with other focused portions of other beams near the focal length in order to inhibit noise.

In many embodiments, the plurality of light sources is arranged in a light source array and the plurality of spot generating lenses is arranged in a spot generator microlens array. The light source array and the spot generator microlens array can be arranged to provide an extended light source and inhibit Talbot artifact.

In many embodiments, one or more wavelengths of said each of the plurality of light sources overlaps with one or more wavelengths of other light sources of the plurality of light sources. Each of the plurality of light sources may comprise a full width half maximum bandwidth of wavelengths overlapping with full width half maximum of wavelengths of other light sources of the plurality of light sources. Each of the plurality of light sources may comprise a full width half maximum bandwidth of no more than about 2 nm overlapping with the full width half maximum bandwidth of said other light sources of the plurality.

In many embodiments, each of the plurality of light sources does not overlap with wavelengths of other light sources of the plurality.

In many embodiments, the apparatus further comprises a plurality of homogenizing microlenses aligned with the plurality of light sources to homogenize an energy distribution profile of said each of the plurality of light beams at the microlens array. Each of the plurality of homogenizing microlenses may comprise an optical surface shaped to homogenize the energy distribution profile, the optical surface comprising one or more of an aspheric refractive optical surface, a diffractive optical surface or a holographic optical surface. The energy distribution profile may comprise a substantially uniform energy profile comprising a maximum value and a minimum value within about 25% of a mean value of the energy profile distribution provided to the plurality of spot generating lenses. The maximum value and the minimum value can be within about 10% of the mean value of the energy profile distribution.

In many embodiments, each light source of the plurality comprises a similar polarization angle to within about 10% of other light sources of the plurality. The substantially similar polarization angle can be within about 5% of other light sources of the plurality.

In many embodiments, the apparatus comprises a detector array and circuitry coupled to the plurality of light sources and the detector array, wherein the circuitry comprises instructions to generate the plurality of light beams at predetermined time intervals.

In many embodiments a method of measuring an object comprises generating a plurality of light beams and focusing the plurality of light beams to a plurality of focused spots with a plurality of spot generating lenses. Each of the plurality of focused spots may comprise a focused portion of each of the plurality of light beams, said focused portion of each of the plurality of beams overlapping with other focused portions of other beams in order to define said each of the plurality of focused spots and inhibit noise. The plurality of spot generating lenses can be separated from the plurality of light sources with a separation distance, said each of the plurality of lenses comprising a focal length, said each of the plurality of light sources comprising a spacing distance from adjacent sources of the plurality of light sources and wherein said separation distance, said focal length and said spacing distance are arranged to overlap said focused portion of each of the plurality of beams with other focused portions of other beams near the focal length in order to inhibit noise.

In many embodiments, a light source for illuminating an optical system comprises an array of vertical cavity surface emitting lasers (VCSELs) operatively connectable to a power source and wherein the VCSELs have similar polarization.

In many embodiments the VCSELs emit similar wavelengths.

In many embodiments, the VCSELs comprise optical resonators that are not synchronized with each other.

In many embodiments, the beams comprise similar wavelengths.

In many embodiment, the array of VCSELs comprise a common die shaped to provide the array.

In many embodiments, a method comprises providing an array of vertical cavity surface emitting lasers (VCSELs) operatively connectable to a power source and wherein the VCSELs have similar polarization.

In many embodiments, a light source for illuminating an optical system comprises an array of VCSELs operatively connectable to a power source and a homogenizing lens array, comprising a plurality of homogenizing lenses, each VCSEL emitter having a respective homogenizing lens of the plurality in registry therewith.

In many embodiments, second lens array to receive a homogenized beam and form an array of focused beams.

In many embodiments, the array of VCSELs comprises single substrate and a common light emitting material in order to provide similar overlapping wavelengths for each laser of the array, and wherein each laser comprises a full width half maximum wavelength bandwidth overlapping with at least about 50% of a full width half maximum of each other laser of the array.

In many embodiments, a method comprises providing an array of VCSELs operatively connectable to a power source and providing a homogenizing lens array, in which the homogenizing array comprises a plurality of homogenizing lenses, each VCSEL emitter having a respective homogenizing lens of the plurality in registry therewith.

In many embodiments, the array of VCSELs comprises a homogenizing microlens array, which includes a dedicated homogenizing lens in registry with each of the VCSELs. In many embodiments, the result is that the aggregate extended source laser beam produced by the VCSEL array has a top-hat profile, which is of particular advantage when coupled to a second microlens array that generates the plurality of laser beams, since all the microlenses of the second microlens array receive uniform light from the laser source.

In many embodiments, The VCSEL array is arranged as a hexagonal array. The array may comprise a number of VCSELs within a range from about 30-100 VCSELs, for example.

In many embodiments, the VCSELs are not optically synchronized with one another, and thus, since each VCSEL fully illuminates all of the microlenses of the second microlens array (that generates the plurality of beams), there is natural speckle reduction.

In many embodiments, all the individual VCSELs of the array have substantially the same polarization, so that the full homogenized beam is polarized with the same polarity, thereby enabling the full beam power to be transmitted to the object being scanned, and the full reflected beam to be received by the detector via the polarized beam splitter. In many embodiments, there is no need to add a polarizer downstream of the VCSEL array which would otherwise result in losses as part of the light energy would be lost due to the polarizer, resulting in a weaker homogenized beam, or the requirement for a larger VCSEL array, which can lead to other problems or undesired design constraints.

In many embodiments, the VSCEL array comprises one or more characteristics suitable for use in combination with a confocal scanning system. In many embodiments, the array of VCSELs emitters is arranged to form an effective extended source. The array may comprise a narrow spectral bandwidth, for example about 2 nm. Each of the VSCELs can emit substantially the same wavelength, for example with a bandwidth of about 1 nm overlapping with other lasers of the array. Alternatively, each laser of the array can emit a different wavelength, for example. In many embodiments, the VCSEL array provides sufficiently intense, dense and collimated light, suitable for combination with a confocal scanning system.

In many embodiments, the VSCEL array emits visible red light, for example.

In many embodiments, the polarization ratio is about 20:1, for example.

Figure 1B:
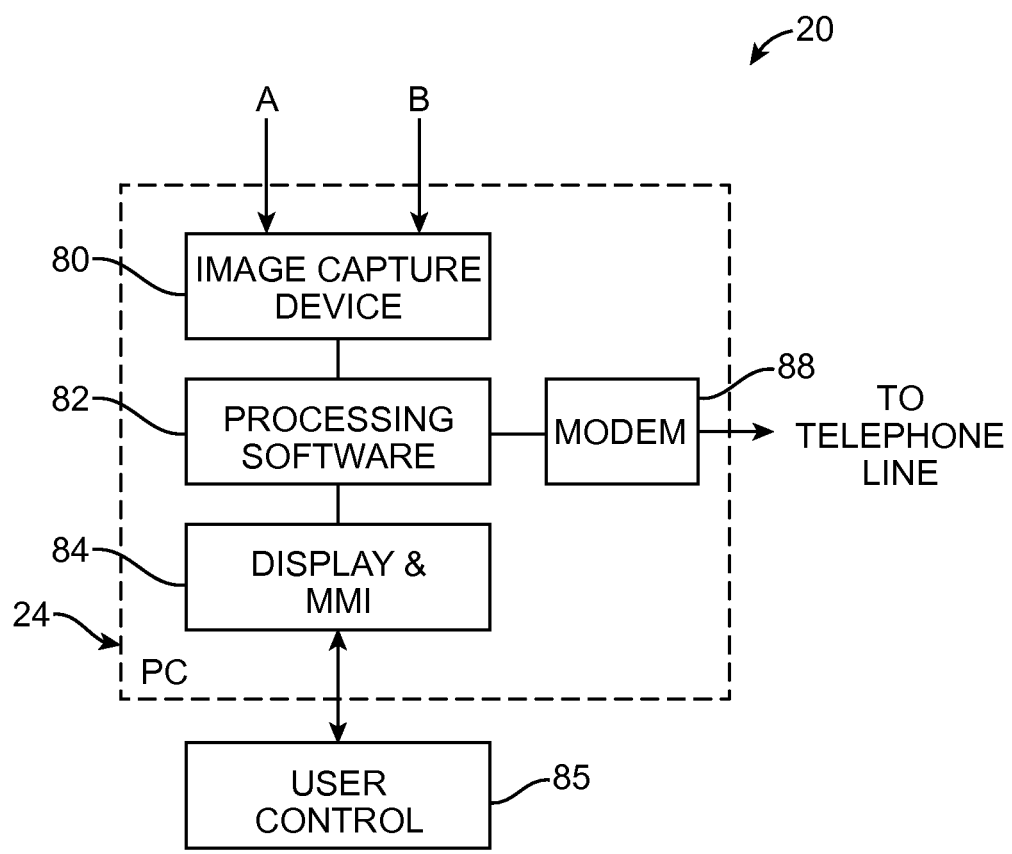

Turning now to the drawings, in which like numbers and/or words designate like elements in the various figures, FIGS. 1A and 1B illustrate an apparatus 20 for measuring surface topography optically. The apparatus 20 includes an optical device 22 coupled to a processor 24. The embodiment illustrated in FIG. 1 is particularly useful for measuring surface topography of a patient's teeth 26. For example, the apparatus 20 can be used to measure surface topography of a portion of the patient's teeth where at least one tooth or portion of tooth is missing to generate surface topography data for subsequent use in design and/or manufacture of a prosthesis for the patient (e.g., a crown or a bridge). It should be noted, however, that the invention is not limited to measuring surface topography of teeth, and applies, mutatis mutandis, also to a variety of other applications of imaging of three-dimensional structure of objects (e.g., for the recordal of archeological objects, for imaging of a three-dimensional structure of any suitable item such as a biological tissue, etc.).

The optical device 22 includes, in the illustrated embodiment, a semiconductor laser array unit 28 emitting a laser light, as represented by arrow 30. The light passes through a polarizer 32, which causes the light passing through the polarizer 32 to have a certain polarization. The light then enters into an optic expander 34, which increases the diameter of the light beam 30. The light beam 30 then passes through a module 38, which can, for example, be a grating or a micro lens array that splits the parent beam 30 into a plurality of light beams 36, represented here, for ease of illustration, by a single line.

The optical device 22 further includes a partially transparent mirror 40 having a small central aperture. The mirror 40 allows transfer of light from the laser array unit 28 through the downstream optics, but reflects light travelling in the opposite direction. It should be noted that in principle, rather than a partially transparent mirror, other optical components with a similar function may be used (e.g., a beam splitter). The aperture in the mirror 40 improves the measurement accuracy of the apparatus. As a result of this mirror structure, the light beams produce a light annulus on the illuminated area of the imaged object as long as the area is not in focus. The annulus becomes a sharply-focused illuminated spot when the light beam is in focus relative to the imaged object. Accordingly, a difference between the measured intensity when out-of-focus and in-focus is larger. Another advantage of a mirror of this kind, as opposed to a beam splitter, is that internal reflections that occur in a beam splitter are avoided, and hence the signal-to-noise ratio is greater.

The optical device 22 further includes confocal optics 42, typically operating in a telecentric mode, relay optics 44, and an endoscopic probe member 46. In many embodiments, the confocal optics 42 is configured to avoid distance-introduced magnification changes and maintain the same magnification of the image over a wide range of distances in the Z direction (the Z direction being the direction of beam propagation). In many embodiments, the relay optics 44 is configured to maintain a certain numerical aperture of the light beam's propagation.

The endoscopic probe member 46 can include a light-transmitting medium, which can be a hollow object defining within it a light transmission path or an object made of a light transmitting material (e.g., a glass body or tube). The light-transmitting medium may be rigid or flexible (e.g., fiber optics). In many embodiments, the endoscopic probe member 46 includes a mirror 95 of the kind ensuring a total internal reflection and directing the incident light beams towards the patient's teeth 26. The endoscope 46 thus emits a plurality of incident light beams 48 impinging on to the surface of the patient's teeth 26.

In many embodiments, the distance between the endoscopic probe member 46 and the patient's teeth 26 is determined by measuring one or more characteristics of returning light beams 54 generated by illuminating the teeth 26 with the incident light beams 48. Such characteristics can include, for example, intensity, wavelength, polarization, phase shift, interference, and/or dispersion of the returning light beams 54. Any description herein relating to light intensity can also be applied to other suitable characteristics of light, and vice-versa. The measurements of the characteristic(s) can be used to detect whether the incident light beams 46 are focused on the surface of the teeth 26 and thereby determine the distance between the endoscopic probe member 46 and the teeth 26.

For example, as depicted in FIGS. 1A and 1B, the distance can be determined based on measured light intensities. The incident light beams 48 form an array of light beams arranged in an X-Y plane, relative to a Cartesian reference frame 50, and propagating along the Z axis. When the incident light beams 48 are incident upon an uneven surface, resulting illuminated spots 52 are displaced from one another along the Z axis, at different $(X_i, Y_i)$ locations. Thus, while an illuminated spot 52 at one location may be in focus for a given focal length produced by the confocal optics 42, illuminated spots 52 at other locations may be out-of-focus. Therefore, the light intensity of the returned light beams of the focused spots will be at its peak, while the light intensity at other spots will be off peak. Thus, for each illuminated spot, a plurality of measurements of light intensity are made at different positions along the Z-axis and for each of such $(X_i, Y_i)$ locations, typically the derivative of the intensity over distance (Z) will be made, and the $Z_i$ yielding maximum derivative, $Z_0$, will be the in-focus distance. As pointed out above, where, as a result of use of the mirror with aperture 40, the incident light forms a light disk on the surface when out of focus and a sharply-focused light spot only when in focus, the distance derivative will be larger when approaching in-focus position thus increasing accuracy of the measurement.

The light reflected from each of the illuminated spots 52 includes a beam travelling initially in the Z axis in the opposite direction of the optical path traveled by the incident light beams. Each returned light beam 54 corresponds to one of the incident light beams 36. Given the unsymmetrical properties of mirror 40, the returned light beams 54 are reflected in the direction of a detection assembly 60. The detection assembly 60 includes a polarizer 62 that has a plane of preferred polarization oriented normal to the polarization plane of polarizer 32. The returned polarized light beam 54 pass through an imaging optic 64, typically a lens or a plurality of lenses, and then optionally through an array of pinholes 66. Each returned light beam 54 may pass at least partially through a respective pinhole of the array of pinholes 66. A charge-coupled device (CCD) sensor array 68 includes a matrix of sensing elements. In many embodiments, each sensing element represents a pixel of the image and each sensing element corresponds to one pinhole in the array 66.

The sensor array 68 is connected to an image-capturing module 80 of the processor unit 24. The light intensity measured by each of the sensing elements of the sensor array 68 is analyzed, in a manner described below, by the processor 24.

The optical device 22 includes a control module 70 that controls operation of the semi-conducting laser 28. The control module 70 can be used in conjunction with any suitable mechanism or configuration for controlling the focal positions of the incident light beams 36. For example, in many embodiments, a motor 72 is drivingly coupled with the confocal optics 42 so as to scan the focus of the light beams through a range of focal depths along the Z axis. In a single sequence of operation, the control unit 70 induces motor 72 to reconfigure the confocal optics 42 to change the focal plane location and then, after receipt of a feedback that the location has changed, the control module 70 induces the laser 28 to generate a light pulse. The control module 70 synchronizes the operation of the image-capturing module 80 with the operation of the confocal optics 42 and the laser 28 during acquisition of data representative of the light intensity from each of the sensing elements. Then, in subsequent sequences, the confocal optics 42 causes the focal plane to change in the same manner and intensity data acquisition continues over a range of focal lengths.

The intensity data is processed by the processor 24 per processing software 82 to determine relative intensity in each pixel over the entire range of focal planes of confocal optics 42. As explained above, once a certain light spot is in focus on the three-dimensional structure being measured, the measured intensity of the returning light beam will be maximal. Thus, by determining the $Z_i$ corresponding to the maximal light intensity or by determining the minimum derivative of the light intensity, for each pixel, the relative in-focus focal length along the Z axis can be determined for each light beam. Thus, data representative of the three-dimensional topography of the external surfaces of the teeth is obtained. A resulting three-dimensional representation can be displayed on a display 84 and manipulated for viewing (e.g., viewing from different angles, zooming-in or out) by a user control module 85 (typically a computer keyboard). In addition, the data representative of the surface topology can be transmitted through an appropriate data port such as, for example, a modem 88 or any suitable communication network (e.g., a telephone network) to a recipient (e.g., to an off-site CAD/CAM apparatus).

By capturing, in this manner, relative distance data between the probe and the structure being measured from two or more angular locations around the structure (e.g., in the case of a teeth segment, from the buccal direction, lingual direction and/or optionally from above the teeth), an accurate three-dimensional representation of the structure can be generated. The three-dimensional data and/or the resulting three-dimensional representation can be used to create a virtual model of the three-dimensional structure in a computerized environment and/or a physical model fabricated in any suitable fashion (e.g., via a computer controlled milling machine, a rapid prototyping apparatus such as a stereo lithography apparatus).

As already pointed out above, a particular and preferred application is imaging of a segment of teeth having at least one missing tooth or a portion of a tooth. The resulting three-dimensional surface topography data can, for example, be used for the design and subsequent manufacture of a crown or any other prosthesis to be fitted into this segment.

Figure 2A:
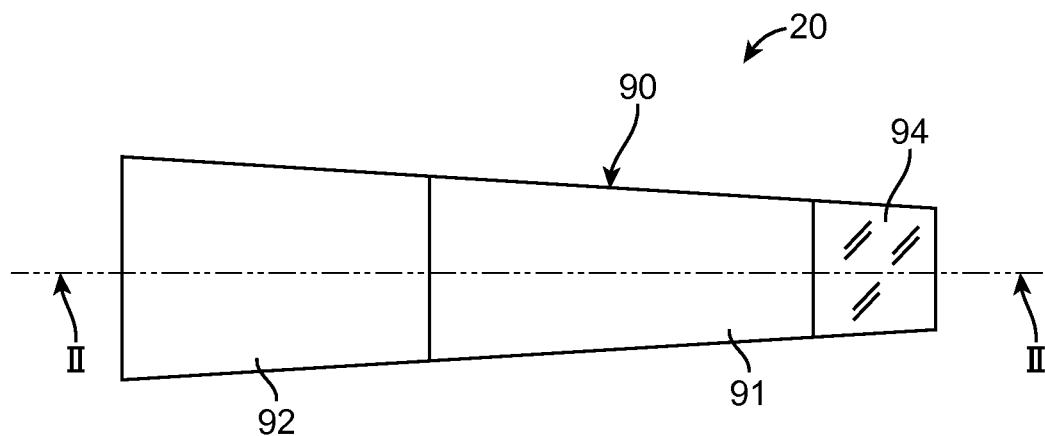
FIG. 2A illustrates a top view of a probing member in accordance with many embodiments.
Figure 2B:
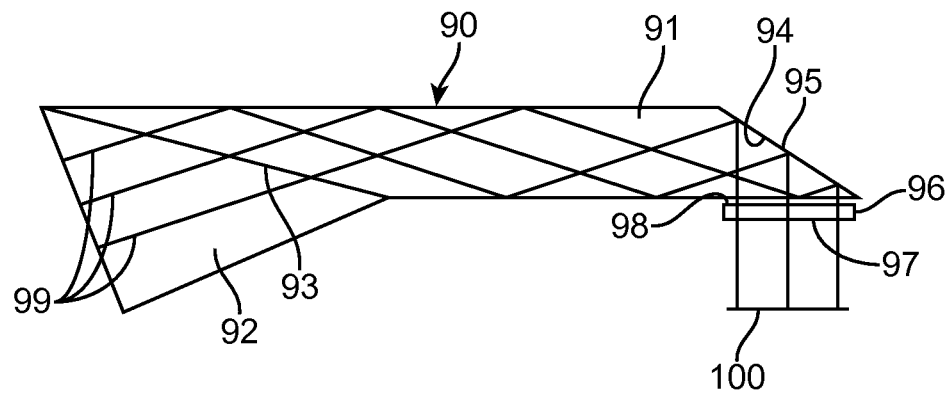
FIG. 2B illustrates a longitudinal cross-section through the probing member of FIG. 2A, depicting exemplary rays passing therethrough.

Referring now to FIGS. 2A and 2B, a probing member 90 is illustrated in accordance with many embodiments. The probing member 90 can be made of a light transmissive material (e.g., glass, crystal, plastic, etc.) and includes a distal segment 91 and a proximal segment 92, tightly glued together in an optically transmissive manner at 93. A slanted face 94 is covered by a reflective mirror layer 95. A transparent disk 96 (e.g., made of glass, crystal, plastic, or any other transparent defining a sensing surface 97 is disposed along the optical path distal to the mirror layer 95 so as to leave an air gap 98 between the glass disk 96 and the distal segment 91. The transparent disk 96 is fixed in position by a holding structure (not shown). Three light rays 99 are represented schematically. As can be seen, the light rays 99 reflect from the walls of the probing member 90 at an angle in which the walls are totally reflective, reflect from the mirror layer 95, and then propagate through the sensing face 97. The light rays 99 are focused on a focusing plane 100, the position of which can be changed by the confocal optics 42.

Figure 3:
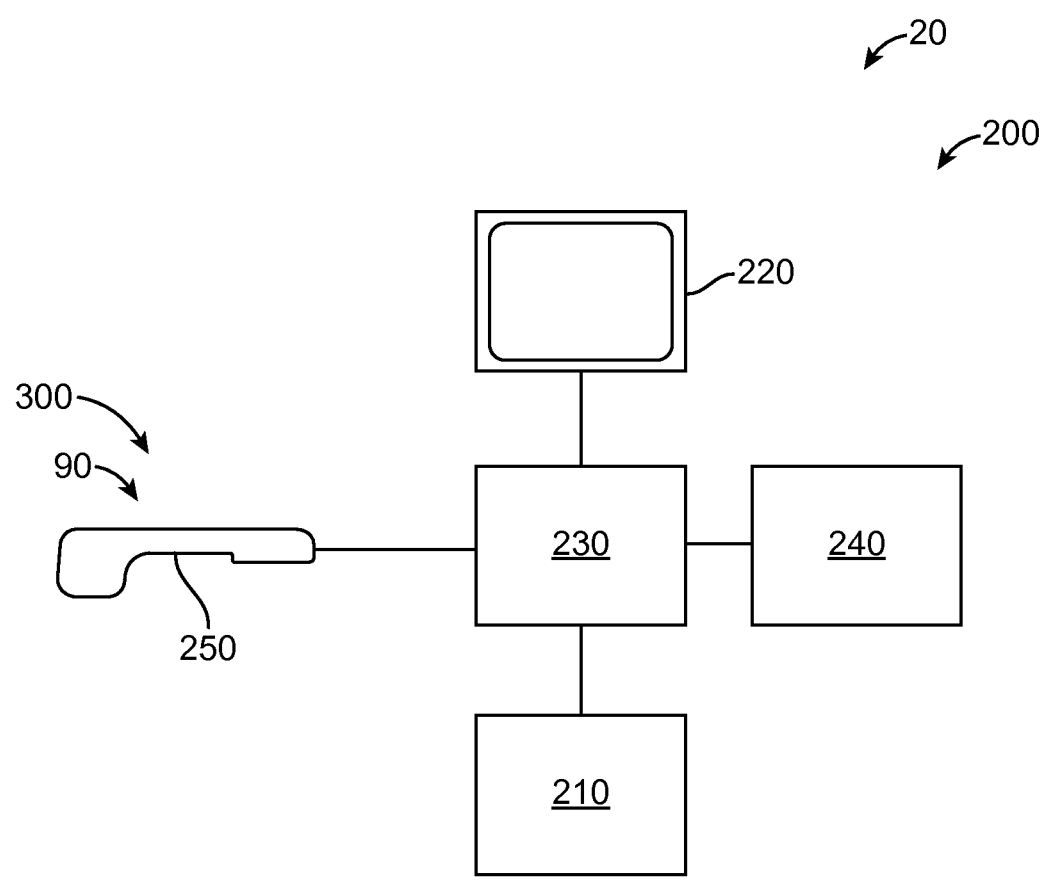
FIG. 3 illustrates a system for scanning an intraoral cavity, in accordance with many embodiments.

FIG. 3 illustrates the main elements of a system 200 for scanning an intraoral cavity, in accordance with many embodiments. The system 200 includes an input unit 210 (e.g., a keyboard, mouse, joystick, tablet, or touch screen), a display or output module 220 (e.g. a screen, monitor, or printer), a processing unit 230 (e.g., comprising one or more processors such as a CPU), and a memory 240. A handheld scanner 250 (e.g., an intraoral scanner) is operatively connected to the system 200. Any suitable scanning system or device for obtaining 3D topographical data of the intraoral cavity can be used for the scanner 250, such as the optical device 22 and/or the optical system 300 (see FIG. 4). For example, the scanner 250 can be a "point-and-shoot" scanner configured such that each scan event is initiated by a specific user input command (e.g., a button press, mouse click, etc). In such embodiments, each scan can be performed while the scanner 250 is held stationary at a desired position and orientation. As another example, the scanner 250 can be a "continuous scanner" configured to continuously obtain scan data without requiring user input to specifically initiate each scan (e.g., based on control signals produced by the processing unit 230). In such embodiments, scanning can be performed continuously or at predetermined time intervals as the scanner 250 moves through a plurality of positions and orientations relative to the intraoral cavity. Scan data collected by the scanner 250 can be processed by the processing unit 230 to reconstruct the surface topography of the intraoral cavity, thereby generating a 3D digital model of the intraoral cavity. The surface topography data can be presented to the user (e.g., as a 3D graphical representation on the display 220) and/or stored for subsequent applications (e.g., in the memory 240).

In many embodiments, the intraoral scanning systems provided herein include a viewfinder that provides two-dimensional image data of the intraoral cavity corresponding to the field of view of the scanner. In many embodiments, the viewfinder and scanner are optically aligned such that the field of view of the viewfinder is the same or similar to the field of view of the scanner. The viewfinder images can be displayed to a user in order to guide the scanning procedure and can be updated as the scanner moves to reflect changes in the scanner's field of view. Accordingly, the user can adjust the position and orientation of the scanner based on the displayed viewfinder images in order to ensure satisfactory scanning coverage of the targeted portion of the intraoral cavity.

The approaches provided herein can be used with any suitable scanner and viewfinder system. The viewfinder can include any suitable imaging device operable to provide images corresponding to the field of view of the scanner, such as a camera suitable for capturing monochromatic or color image data. For example, the viewfinder images may represent the field of view of the scanner, e.g., in terms of viewing angle, coverage area, etc. The viewfinder field of view may be similar to or larger than the scanner field of view, such that the viewfinder images represent the entirety of the field of view of the scanner. Alternatively, the viewfinder field of view may be smaller than or partially overlapping with the scanner field of view, such that the viewfinder images represent a subset of the field of view of the scanner. In many embodiments, the viewfinder is adapted to record image data in real time, such that the viewfinder images are continuously displayed and updated as the scanner is moved. For example, the viewfinder can include a camera with a suitable video capture rate for real-time display. Alternatively, the viewfinder can record image data at a video capture rate different than the video display rate.

Figure 4:
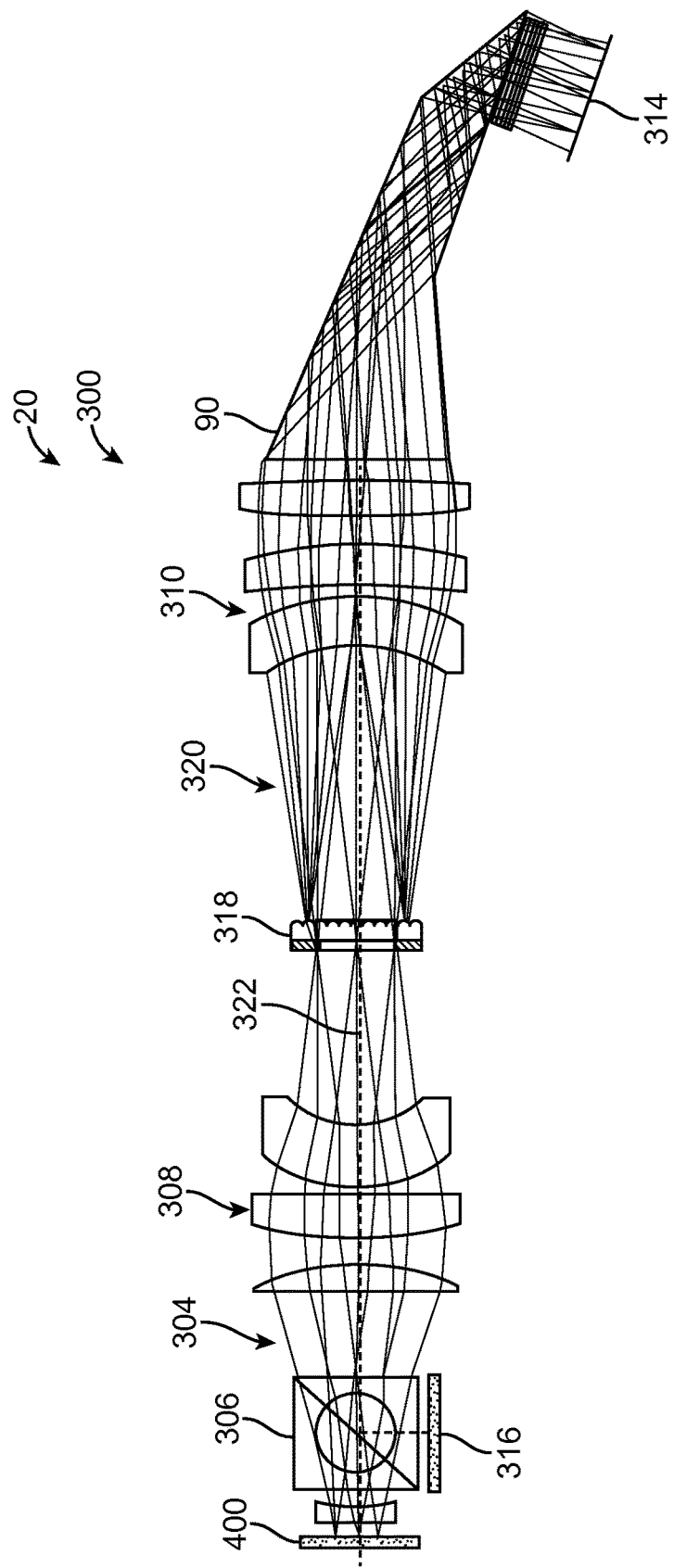
FIG. 4 illustrates an optical system with aligned scanner and viewfinder optics, in accordance with many embodiments.

FIG. 4 illustrates an optical system 300 with aligned scanner and viewfinder optics, in accordance with many embodiments. At least some of the elements of the optical system 300 can be combined with the other systems and devices described herein, such as the apparatus 20 and/or the system 200. In many embodiments, at least some of the components of the optical system 300 form part of an intraoral scanning device, such as the handheld scanner 250. In the system 300, the components of the scanner and viewfinder are integrated into a single device, such at least some portions of the optical path of the scanner overlap with the optical path of the viewfinder and at least some optical components of the system 300 are shared between the scanner and viewfinder. The system 300 comprises spot generator 400 that produces a two-dimensional array of light beams 304 (e.g., an array of laser beams) for surface topography scanning. The array of light beams 304 can propagate through a polarizing beam splitter 306, a first set of lens elements 308, a second set of lens elements 310, and a probing member 90 so as to illuminate the surface of a targeted object with a two-dimensional array of light spots. In many embodiments, the array of light beams 304 is focused to a focal plane 314 external to the probing member 90. Light beams reflected from the surface can pass back through the probing member 90 and lens elements 308, 310 and are directed by the beam splitter 306 onto an detector unit 316 (e.g., sensor array 68). The detector unit 316 can include a plurality of sensor elements used to measure characteristics of the returning light (e.g., light intensity) in order to determine the surface topography, as previously described herein.

The system 300 also includes a viewfinder illumination unit 318 that provides a plurality of light beams 320 for generating viewfinder image data. For example, the viewfinder illumination unit 318 can include a plurality of LEDs. The LEDs can be arranged in a ring configuration, with the central aperture of the ring sized to permit light beams of the array 304 and returning light beams from the object surface to pass through. The light beams 320 produced by the viewfinder illumination unit 318 can propagate through the second set of lens elements 310 and the probing member 90 to illuminate the object surface. Light reflected from the surface can pass back through the optics and onto the sensor elements of the detector unit 316, as described above. The sensor data can subsequently be processed using techniques known to those of skill in the art to provide viewfinder images. Notably, the system 300 can utilize a single detector unit 316 to generate scan data and viewfinder image data, rather than having separate detector units for scanning and image capture. In many embodiments, the scanner and viewfinder optics are optically aligned so as to share a common optical axis 322, such that the field of view of the scanner is the same or similar to the field of view of the viewfinder and the viewfinder images provided by the viewfinder correspond to the field of view of the scanner.

In many embodiments, the system 300 can utilize a single detector unit 316 to generate scan data and viewfinder image data, rather than having separate detector units for topography scanning and image capture. Alternatively, the system 300 may comprise separate detectors for generating scanning data from the array of light beams 304 and for generating viewfinder image data, in which the scanner and viewfinder optical axes are optically aligned, for example.

The viewfinder illumination unit 318 can be adapted to provide monochromatic or polychromatic illumination (e.g., via colored LEDs). In many embodiments, the illumination unit 318 sequentially illuminates the targeted object with different wavelengths (e.g., red, green, and blue wavelengths) and the detector unit 316 obtains a monochromatic image corresponding to each wavelength. The different monochromatic images can be subsequently be processed and merged to provide a composite color image of the object. Optionally, the system 300 can include chromatic dispersion optics along the optical path between the illumination unit 318 and the imaged object, such that each wavelength of light is focused to a different focal depth. Accordingly, the focused and unfocused areas of each monochromatic image may differ based on the particular illumination wavelength used. Suitable image processing algorithms can be used to identify the focused areas of each image in order to increase the clarity and precision of the final composite image.

An intraoral scanning procedure may involve capturing topographical scan data of multiple portions of the patient's intraoral cavity. As previously described, the user can view the image data provided by the viewfinder (e.g., via a graphical interface provided on a display, as described in greater detail below) in order to determine which portions of the intraoral cavity are included in the current field of view of the scanner. Furthermore, suitable guidance mechanisms can be implemented to indicate to the user which portions of the cavity have already been scanned in order to improve scanning efficiency and reduce unnecessary rescanning. These guidance mechanisms can include visual indicators provided on a display (e.g., as an overlay on top of the current viewfinder image) that permit the user to rapidly and accurately assess whether the current field of view is situated at an appropriate location relative to the areas of previous scan coverage. The user can then position and orient the field of view of the scanner accordingly so as to scan targeted portions of the intraoral cavity while reducing the overlap with previously scanned areas. In many embodiments, the visual indicators can be updated or adjusted according to the scanning progress and scanner movement, thereby providing real-time or near real-time scanning guidance.

Figure 5:
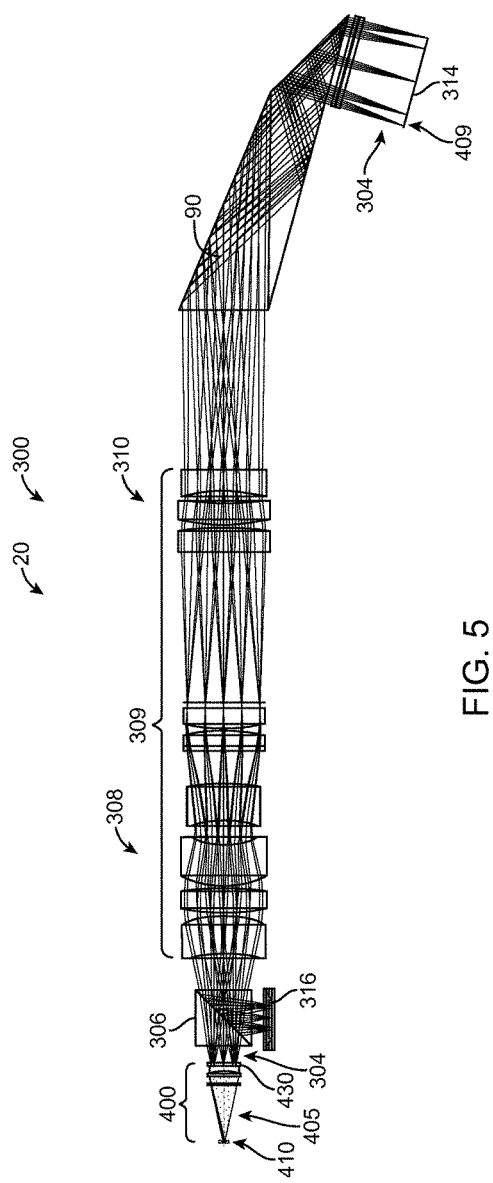
FIG. 5 shows an optical system comprising a spot generator in accordance with many embodiments.

FIG. 5 shows optical system 300 comprising a spot generator 400 comprising a VCSEL array 410. The VCSEL array generates a plurality of light beams. The plurality of light beams 405 from the VCSEL array travel a distance such that the plurality of beams overlap. The plurality of overlapping light beam 405 can illuminate a spot generator 400. In many embodiments, the spot generator 400 comprises a microlens array 430 to generate light beams 304 from the overlapping light beams incident on the microlens array. The light beams 304 are directed to the beam splitter 306 and focusing optics 309 comprising lens elements 308 and lens elements 310 as described herein. The light beams 304 are received with probe 90 to measure the surface as described herein.

In many embodiments, the plurality of light beams 304 is focused to a plurality of spots 409 along focal surface such as focal plane 314. Each of the plurality of spots 409 comprises light from a plurality of light sources in order to smooth the energy profile of the spot and decrease noise.

FIG. 6 shows components of spot generator 400 as in FIG. 5. The spot generator 400 may comprise a microlens array 420, a preferably low attenuation linear polarizer 434, a collimating lens 432, in combination with the VCSEL array 410 and spot generating microlens array 430, for example. The VCSEL array 410 comprises a plurality of light sources distributed in relation to optical axis 322. The VCSEL array 410 comprises an emitting surface 415 from which the light beams are emitted. The VCSEL microlens array is located in close proximity to the VCSEL emitting surface 415. The plurality of light beams from the microlens array 420 can be directed toward a low attenuation polarizing beam splitter 434. The microlens array 420 can be spaced from the microlens array 430 with a sufficient distance such that a far field diffraction pattern of each lens of the VCSEL microlens array 420 is provided to the microlens array 430. In many embodiments, the far field diffraction pattern of the overlapping beams 405 provides a homogenized intensity profile distribution 440 at the microlens array 430.

The collimating lens 432 can be spaced apart from the VCSEL emitting surface 415 with a distance approximately equal to a focal length of the lens 432 such that the lens 432 substantially collimates light received from the VCSEL array.

In many embodiments, each of the lasers of the VCSEL array is similarly polarized with the other lasers of the array such that the low attenuation linear polarizer may not be beneficial. In some embodiments, the low attenuation linear polarizer 434 can be rotated to set an output energy of the spot generator 400, for example.

The spot generating microlens array 430 defines an aperture window 440 having a dimension across 440 sized for components of optical system 300 such as focusing optics 309, probe 90 and detector unit 316 comprising an image sensor array.

FIG. 7 shows a side view of VCSEL array 410 and microlens array 420 to produce a homogenized far field energy distribution profile 440 (not to scale). The VCSEL array 410 comprises a plurality of vertical cavity surface emitting lasers 412. The plurality of lasers 412 comprise a common VCSEL die 416. The plurality of lasers 412 are spaced at regular distances 418 along the die 416.

The homogenizing microlens array 420 comprises a plurality of lenses 422 spaced at regular distances corresponding to distances 418 of the plurality of lasers 412. A plurality of optical axes 423 can extend between the plurality of lasers 412 and the plurality of lenses 422 such that the plurality of lenses are aligned with the plurality of lasers. In many embodiments, each laser of the VCSEL array 410 is aligned with a corresponding lens of the lens array 420. In many embodiments, a center of an aperture of the laser is aligned with a center of the corresponding lens for each laser and lens of the plurality of lasers and lenses. The registration of the microlens array 420 with the VSCEL array 410 allows the laser beams to be overlapped with and provide a uniform energy profile at the spot generator array 430, which may comprise a top hat energy profile.

The homogenizing microlens array 420 can be configured in one or more of many ways to provide the homogenized energy profile. The lenses 422 of the microlens array 420 may comprise lenses having an optical surface shape profile such as an aspheric shape profile in order to provide the homogenized energy distribution profile. Alternatively or in combination, the lenses 422 may comprise diffractive optical surfaces or holographic optical elements, and combinations thereof, for example. Each of the lenses of the array may comprise a concave aspheric profile to provide a substantially uniform intensity pattern with a divergent beam at the collimating lens. In many embodiments the homogenizing microlens array 420 comprises a thickness 424 sufficient to support to the lens array. For illustration purposes in accordance with some embodiments, the far field diffraction profile may comprise a non-uniform energy profile 442.

In many embodiments, the homogenizing microlens array 420 is separated from the spot generator lens array 430 with a distance sufficient to develop a far field diffraction pattern of the plurality of lenses 422 of the array 420 at the spot generating microlens array 430.

The VCEL array 420 can connected to circuitry configured to drive the array in one or more of many ways. For example, the lasers of the array 420 can be connected in parallel so as to turn the lasers on and off together in response to signals from the controller as described herein.

FIG. 8A shows top view of the VCSEL array 410 and microlens array 420 of FIG. 7. The microlens array 420 may comprise a hexagonal array of lenses, although the lenses of the array can be arranged in any configuration suitable for use in accordance with embodiments disclosed herein. The VCSEL array 410 is shown through the window 440 of the microlens array 420.

FIG. 8B shows an enlarged top view of the VCSEL array 410 and microlens array 420 of FIGS. 7 and 8A. The lenses of the microlens array 420 are shown in registration with the lasers of the VCSEL array 410 along axes 423. The plurality of lenses 422 and the plurality of lasers 412 are arranged along corresponding rows. The axes 423 can be arranged along a plurality of rows. The rows can intersect each other at angles such as 120 degrees, for example.

In many embodiments, the VCSEL array 410 is arranged with one or more components of the optical system such as the spot generator array 430, so as to comprise an extended source for each of the measurement beams 304. The extended source can inhibit Talbot artifact and speckle and provide a smoothed energy distribution profile for each of the measurement beams 304.

Figure 9:
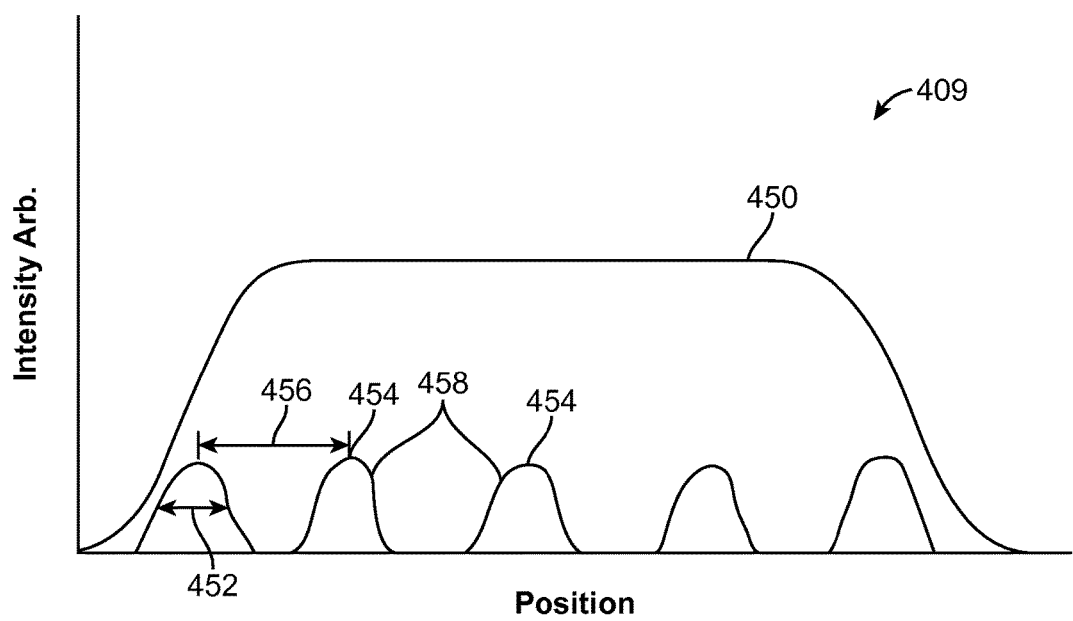
FIG. 9 shows an energy profile of a focused spot of a measurement beam, in accordance with embodiments.

FIG. 9 shows near field and far field energy profiles. In the near field, for example very close to the VCSEL emitters (e.g. a few micrometers), the illumination profiles 458 of the individual emitters do not overlap. At a distance from the VCSEL emitting plane the beams begin to overlap, and the initial overlap can occur a few hundred micrometers from the VCSEL emitter plane. In many embodiments, the far field profiles at distances greater than a few hundred micrometers from the emitter plane comprise substantial overlap such that the individual spots are not readily discernable with the far field overlapped energy profile 450.

The spacing distance 418 of the lasers and the distance from the VSCEL array 410 to the spot generator array 430 can be arranged to substantially overlap the plurality of spots 458 and provide smooth overlapped energy profile 450. The spacing distance 418 corresponds to the separation distance 456 between peaks 454 of the spots close to the array. In many embodiments, the spots comprise substantial overlap such that the spots cannot be resolved from each other when provided together to form profile 450. Each of the spots 458 may comprise a peak 454 and a full width half maximum distance 452 across. In the near field close to the VCSEL emitter plane, the peaks 454 of the spots 458 can be separated by a distance 456 greater than the full width half maximum distance 452, such that the spots are discernible from each other. However, in the far field the full width half maximum of the individual spots is much greater than the separation distance of the emitters such that the individual beams cannot be discerned.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. An apparatus to measure an object, the apparatus comprising:
   a plurality of light sources arranged to generate a plurality of light beams; and
   a plurality of spot generating lenses to focus the plurality of beams to a plurality of focused spots, each of the plurality of focused spots comprising a focused portion of each of the plurality of light beams, said focused portion of each of the plurality of beams overlapping with other focused portions of other beams in order to define said each of the plurality of focused spots and inhibit noise, wherein the plurality of spot generating lenses is separated from the plurality of light sources with a separation distance sufficient to overlap the plurality of light beams at each of the spot generating lenses.

2. An apparatus as in claim 1, wherein the apparatus comprises a scanning confocal apparatus to measure topography of the object in response to scanning of said each of the plurality of focused spots.

3. An apparatus as in claim 1, wherein said each of the plurality of lenses comprises a focal length, and said each of the plurality of light sources comprises a spacing distance from adjacent sources of the plurality of light sources and wherein said separation distance, said focal length and said spacing distance are arranged to overlap said focused portion of each of the plurality of beams with other focused portions of other beams near the focal length in order to inhibit noise.

4. An apparatus as in claim 1, wherein the plurality of light sources is arranged in a light source array and the plurality of spot generating lenses is arranged in a spot generator microlens array and wherein the light source array and the spot generator microlens array are arranged to provide an extended light source and inhibit Talbot noise.

5. An apparatus as in claim 1, wherein one or more wavelengths of said each of the plurality of light sources overlaps with one or more wavelengths of other light sources of the plurality of light sources.

6. An apparatus as in claim 5, wherein said each of the plurality of light sources comprises a full width half maximum bandwidth of wavelengths overlapping with full width half maximum of wavelengths of other light sources of the plurality of light sources.

7. An apparatus as in claim 6, wherein said each of the plurality of light sources comprises a full width half maximum bandwidth of no more than about 2 nm overlapping with said full width half maximum bandwidth of said other light sources of the plurality.

8. An apparatus as in claim 1, wherein wavelengths of said each of the plurality of light sources does not overlap with wavelengths of other light sources of the plurality.

9. An apparatus as in claim 1, the apparatus further comprising:
a plurality of homogenizing microlenses aligned with the plurality of light sources to homogenize an energy distribution profile of said each of the plurality of light beams at the microlens array.

10. An apparatus as in claim 9, wherein each of the plurality of homogenizing microlenses comprises an optical surface shaped to homogenize the energy distribution profile, the optical surface comprising one or more of an aspheric refractive optical surface, a diffractive optical surface or a holographic optical surface.

11. An apparatus as in claim 9, wherein the energy distribution profile comprises a substantially uniform energy profile comprising a maximum value and a minimum value within about 25% of a mean value of the energy profile distribution provided to the plurality of spot generating lenses.

12. An apparatus as in claim 11, wherein the maximum value and the minimum value are within about 10% of the mean value of the energy profile distribution.

13. An apparatus as in claim 1, wherein each light source of the plurality comprises a similar polarization angle to within about 10% of other light sources of the plurality.

14. An apparatus as in claim 1, further comprising:
a detector array; and
circuitry coupled to the plurality of light sources and the detector array, wherein the circuitry comprises instructions to generate the plurality of light beams at predetermined time intervals.

15. A method of measuring an object, the method comprising:
generating a plurality of light beams; and
focusing the plurality of light beams to a plurality of focused spots with a plurality of spot generating lenses separated from the plurality of light sources with a separation distance sufficient to overlap the plurality of light beams at each of the spot generating lenses, wherein each of the plurality of focused spots comprises a focused portion of each of the plurality of light beams, said focused portion of each of the plurality of beams overlapping with other focused portions of other beams in order to define said each of the plurality of focused spots and inhibit noise.

16. A method as in claim 15, wherein said each of the plurality of lenses comprises a focal length, said each of the plurality of light sources comprises a spacing distance from adjacent sources of the plurality of light sources and wherein said separation distance, said focal length and said spacing distance are arranged to overlap said focused portion of each of the plurality of beams with other focused portions of other beams near the focal length in order to inhibit noise.

* * * * *